United States Patent
Herz et al.

(10) Patent No.: US 8,936,588 B2
(45) Date of Patent: Jan. 20, 2015

(54) DEVICE AND METHOD FOR PREVENTION AND TREATMENT OF DEEP VENOUS THROMBOSIS

(75) Inventors: Frederick Stephan Michael Herz, Warrington, PA (US); Frederick A Reichle, Warrington, PA (US)

(73) Assignee: Fred Herz Patents, LLC, Milton, WV (US)

( * ) Notice: Subject to any disclaimer, the term of this patent is extended or adjusted under 35 U.S.C. 154(b) by 1747 days.

(21) Appl. No.: 10/253,231

(22) Filed: Sep. 23, 2002

(65) Prior Publication Data

US 2003/0069528 A1    Apr. 10, 2003

Related U.S. Application Data

(60) Provisional application No. 60/323,589, filed on Sep. 21, 2001.

(51) Int. Cl.
| | |
|---|---|
| *A61M 31/00* | (2006.01) |
| *A61B 17/00* | (2006.01) |
| *A61H 7/00* | (2006.01) |
| *A61H 19/00* | (2006.01) |
| *A61H 9/00* | (2006.01) |

(52) U.S. Cl.
CPC .......... *A61H 9/0078* (2013.01); *A61H 2205/12* (2013.01)
USPC .................... 604/507; 606/202; 601/151

(58) Field of Classification Search
USPC ............ 604/500, 506–510; 602/5, 12, 26–29; 606/201–204; 601/148, 149, 151, 152
See application file for complete search history.

(56) References Cited

U.S. PATENT DOCUMENTS

| | | | | |
|---|---|---|---|---|
| 3,927,660 | A | * | 12/1975 | Tegtmeyer ..................... 600/431 |
| 4,041,940 | A | * | 8/1977 | Frankel et al. .................. 602/26 |
| 4,181,982 | A | * | 1/1980 | Segovia ............................ 2/239 |
| 4,494,536 | A | * | 1/1985 | Latenser ....................... 128/882 |
| 4,941,458 | A | * | 7/1990 | Taheri ........................... 601/152 |
| 5,254,087 | A | * | 10/1993 | McEwen ......................... 604/66 |
| 5,354,260 | A | * | 10/1994 | Cook .............................. 602/13 |
| 5,584,798 | A | * | 12/1996 | Fox ............................... 601/152 |
| 5,669,872 | A | * | 9/1997 | Fox ............................... 601/152 |
| 5,741,295 | A | * | 4/1998 | McEwen ....................... 606/202 |
| 6,158,051 | A | * | 12/2000 | Belzidsky ........................... 2/22 |
| 6,290,662 | B1 | * | 9/2001 | Morris et al. ................. 601/149 |

(Continued)

OTHER PUBLICATIONS

Abbott E C, Gornall A G, Sutherland D J A, Laidlaw J C, Stiefel M. The influence of a heparin-like compound on hypertension electrolytes and aldosterone in man Can Med Assoc J 1966;94:1155-1164.

(Continued)

*Primary Examiner* — Nathan R Price
(74) *Attorney, Agent, or Firm* — Baker & Hostetler LLP

(57) ABSTRACT

In order to inhibit thrombotic processes locally rather than systemically, higher levels of antithrombotic drugs in the deep veins of the legs than in the systemic circulation are obtained using devices and methods that provide venous cannulation in the dorsum of the foot of a patient while applying pressure to the foot proximal to the venous cannulation, potentially as far up the leg as the knee, in an amount sufficient to compress the superficial veins and divert the venous drainage in the deep venous system into the venous plexus.

5 Claims, 5 Drawing Sheets

(56) References Cited

U.S. PATENT DOCUMENTS

2002/0107504 A1* 8/2002 Gordon .................. 604/507
2002/0143280 A1* 10/2002 Souney et al. .................. 602/32

OTHER PUBLICATIONS

Adelson J, Steer M L, Glotzer D J, Skillman J J, Simon M, Salzman E W. Thromboembolism after insertion of the Mobin-Uddin caval filter Surgery 1980,87:184-189.

Alarcon-Segovia D, Deleze M, Oria C V, Sanchez-Guerrero, J, Gomez-Pacheco L, Cabiedes J, Fernandez L, Ponce de Leon S. Antiphospholipid antibodies and the antiphospholipid syndrome in systemic lupus erythematosus: a prospective analysis of 500 consecutive patients. Medicine (Baltimore). 1989;68:353-365.

Alderson P O, Rujanavech N, Sicker-Walker R H, McKnight R C The role of .sup.133Xe ventilation studies in the scintigraphic detection of pulmonary embolism. Radiology. 1976;120:633-640.

Allaart C F, Aronson D C, Ruys T, Rosendaal F R, van Bockel J H, Bertina R M, Briet E. Hereditary protein S deficiency in young adults with arterial occlusive disease. Thromb Haemost. 1990;64:206-210.

Alperin N, Babu S, Weinstein A. Acute adrenal insufficiency and the antiphospholipid syndrome. Ann Intern Med. 1989;111:950. Letter.

Altman R, Rouvier J, Gurfinkel E, D'Ortencio O, Manzanel R, de La Fuente L, Favaloro R G. Comparison of two levels of anticoagulant therapy in patients with substitute heart valves. J Thorac Cardiovasc Surg. 1991;101:427-431.

Amiral J, Bridey F, Dreyfus M, Vissoc A M, Fressinaud E, Wolf M, Meyer D. Platelet factor 4 complexed to heparin is the target for antibodies generated in heparin-induced thrombocytopenia. Thromb Haemost. 1992;68:95-96. Letter.

Anagrelide Study Group Anagrelide, a therapy for thrombocythemic states: experience in 577 patients. Am J Med 1992,92:69-76.

Anderson D R, Ginsberg J S, Burrows R, Brill-Edwards P. Subcutaneous heparin therapy during pregnancy: a need for concern at the time of delivery. Thromb Haemost. 1991;65:248-250.

Anderson D R, Lensing A W A, Wells P S, Levine M N, Weitz J I, Hirsh J. Limitations of impedance plethysmography in the diagnosis of clinically suspected deep-vein thrombosis. Ann Intern Med. 1993;118:25-30.

Anderson D R, Levine M N. Thrombolytic therapy for the treatment of acute pulmonary embolism. Can Med Assoc J 1992;146:1317-1324.

Anderson D R, O'Brien B J, Levine M N, Roberts R, Wells P S, Hirsh J. Efficacy and cost of low-molecular-weight heparin compared with standard heparin for the prevention of deep vein thrombosis after total hip arthroplasty. Ann Intern Med. 1993;119:1105-1112.

Andersson G, Fagrell B, Holmgren K, Johnsson H, Ljungberg B, Nilsson E, Wilhelmsson S, Zetterquist S. Subcutaneous administration of heparin: a randomised comparison with intravenous administration of heparin to patients with deep-vein thrombosis. Thromb Res. 1982;27:631-639.

Andrew M, David M, Adams N, Ali K, Anderson R, Barnard D, Bernstein M, Brisson L, Cairney B, DeSai D, Grant R, Israels S, Jardine L, Luke B, Massicotte P, Silva M Venous thromboembolic complications (VTE) in children: first analyses of the Canadian Registry of VTE Blood. 1994;83:1251-1257.

Andrew M, Marzinotto V, Pencharz P, Zlotkin S, Burrows P, Ingram J, Adams M, Filler R. A cross-sectional study of catheter-related thrombosis in children receiving total parenteral nutrition at home J Pediatr. 1995,126:358-363.

Ankola P A, Atakent Y S. Effect of adding heparin in very low concentration to the infusate to prolong the patency of umbilical artery catheters. Am J Perinatol. 1993;10:229-232.

Ansell J E, Price J M, Shah S, Beckner R R. Heparin-induced thrombocytopenia. what is its real frequency? Chest. 1985,88:878-882.

Ansell J, Slepchuk N Jr, Kumar R, Lopez A, Southard L, Deykin D. Heparin-induced thrombocytopenia: a prospective study. Thromb Haeniost. 1980;43:61-65.

Appleby D H, Heller M S. Low-dose streptokinase therapy for subclavian vein thrombosis. South Med J 1984;77:536-537.

Asherson R A, Khamashta M A, Ordi-Ros J, Derksen R H, Machin S J B, Barquinero J. Outt H H, Harris E N, Vilardell-Torres M, Hughes G R. The primary antiphospholipid syndrome: major clinical and serological features. Medicine (Baltimore). 1989;68:366-374.

Asherson R A, Merry P, Acheson J F, Harris E N, Hughes G R. Antiphospholipid antibodies: a risk factor for occlusive ocular vascular disease in systemic lupus erythematosus and the "primary antiphospholipid syndrome." Ann Rheum Dis 1989;48:358-361.

Avioli L V. Heparin-induced osteopenia: an appraisal. Adv Exp Med Biol. 1975;52:375-387.

Axelsson C K, Efsen F. Phlebography in long-term catheterization of the subclavian vein: a retrospective study in patients with severe gastrointestinal disorders. Scand J Gastroetiterol. 1978;13:933-938.

Bailey R T Jr, Ursick J A, Heim K L, Hilleman D E, Reich J W. Heparin-associated thrombocytopenia a prospective comparison of bovine lung heparin, manufactured by a new process, and porcine intestinal heparin. Drug Intell Clin Pharm. 1986,20:374-378.

Barradas M A, Mikhailidis D P, Epemolu O, Jeremy J Y, Fonseca V, Dandona P. Comparison of the platelet pro-aggregatory effect of conventional unfractionated heparins and a low molecular weight heparin fraction (CY 222) Br J Haematol. 1987;67:451-457.

Barritt D W, Jordan S C. Anticoagulant drugs in the treatment of pulmonary embolism: a controlled trial. Lancet. 1960;1:1309-1312.

Basu D, Gallus A, Hirsh J, Cade J. A prospective study of the value of monitoring heparin treatment with the activated partial thromboplastin time. N Engl J Med. 1972;287:324-327.

Baxter G M, McKechnie S, Duffy P. Colour Doppler ultrasound in deep venous thrombosis: a comparison with venography. Clin Radiol. 1990;42:32-36.

Becker D M, Philbrick J T, Walker F B IV. Axillary and subclavian venous thrombosis: prognosis and treatment. Arch Intern Med. 1991; 151: 1934-1943.

Becker G J, Holden R W, Rabe F E, Castaneda-Zuniga W R, Sears N, Dilley R S, Glover J L. Local thrombolytic therapy for subclavian and axillary vein thrombosis: treatment of the thoracic inlet syndrome. Radiology. 1983;149:419-423.

Bell W R, Simon T L, DeMets D L. The clinical features of submassive and massive pulmonary emboli. Am J Med. 1977,62.355-360.

Bell W R, Simon T L. A comparative analysis of pulmonary perfusion scans with pulmonary angiograms. Am Heart J. 1976;92:700-706.

Bell W R, Simon T L. Current status of pulmonary thromboembolic disease: pathophysiology, diagnosis, prevention, and treatment. Am Heart J. 1982;103:239-262.

Benifla J L, Madelenat P. Hyperstimulation ofareienne et risque thrombogene. Arteres et Veines. 1990;8:748.

Bentley P G, Kakkar W V, Scully M F, MacGregor L R, Webb P, Chan P, Jones N. An objective study of alternative methods of heparin administration. Thromb Res. 1980;18:177-187.

Bernstein D, Coupey S, Schonberg S K. Pulmonary embolism in adolescents. Am J Dis Child. 1986;140:667-671.

Bertina R M, Koeleman B P, Koster T, Rosendaal F R, Dirven R J, de Ronde H, van der Velden P A, Reitsma R H. Mutation in blood coagulation factor V associated with resistance to activated protein C. Nature. 1994;369:64-67.

Bertrand M, Presant C A, Klein L, Scott E. Iatrogenic superior vena cava syndrome: a new entity Cancer. 1984,54:376-378.

Biello D R, Mattar A G, McKnight R C, Siegel B A. Ventilation-perfusion studies in suspected pulmonary embolism. AJR Am J Roentgenol. 1979;133:1033-1037.

Bjorklid E, Giercksky K E, Prydz H. An immunoradiometric assay for factor III (tissue thromboplastin). Br J Haematol. 1978;39.445-458.

Bjornsson J D, Nash P V. Variability in heparin sensitivity of aPTT reagents. Am J Clint Pathol. 1986,86:199-204.

Bjornsson T D, Wolfram K M, Kitchell B B. Heparin kinetics determined by three assay methods. Clin Pharmacol Ther. 1982;31:104-113.

Bookstein J J, Silver T M. The angiographic differential diagnosis of acute pulmonary embolism. Radiology. 1974,110:25-33.

Bookstein J J. Segmental arteriography by pulmonary embolism. Radiology. 1969;93:1007-1012.

(56) References Cited

OTHER PUBLICATIONS

Borgstrom S, Gelin L E, Zenderfeld B. The formation of vein thrombi following tissue injury Acta Chir Scand Suppl. 1959,247:1-36.
Bosque E, Weaver L Continuous versus intermittent heparin infusion of umbilical artery catheters in the newborn infant. J Pediair. 1986;108 141-143.
Bovill E G, Bauer K A, Dickerman J D, Callas P, West B. The clinical spectrum of heterozygous protein C deficiency in a large New England kindred. Blood. 1989;73:712-717.
Bowie E J W, Thompson J H, Pascuzzi C A, Owen C A Jr. Thrombosis in systemic lupus erythematosus despite circulating anticoagulants J Lab Clin Med. 1963;62:416-430.
Brandjes D P M, Heijboer H, Buller H R, de Rijk M, Jagt H, ten Cate J W Acenocoumarol and heparin compared with acenocoumarol alone in the initial treatment of proximal-vein thrombosis. N Engl J Med. 1992;327:1485-1489.
Brandjes D P M, Heijboer H, de Rijk M, Jagt J, Buller H R, ten Cate J W, Huisman M V. The effect of graded compression stockings on the development of the post-thrombotic syndrome in patients with proximal deep-vein thrombosis. Thromb Haemost. 1991;65(suppl):1131. Abstract.
Branson H E, Katz J, Marble R, Griffin J H. Inherited protein C deficiency and coumarin-responsive chronic relapsing purpura fulminans in a newborn infant Lancet. 1983;2:1165-1168.
Brill-Edwards P, Ginsberg J S, Johnston M, Hirsh J. Establishing a therapeutic range for heparin therapy. Ann Intern Med. 1993;119:104-109.
Broekmans A W, Bertina R M, Loeliger E A, Hofinann V, Klingemann H G. Protein C and the development of skin necrosis during anticoagulant therapy. Thromb Haemost. 1983;49:251.
Broekmans A W, Veltkamp J J, Bertina R M. Congenital protein C deficiency and venous thromboembolism: a study in three Dutch families. N Engl J Med 1983;309:340-344.
Browse N L, Clemenson G, Croft D N. Fibrinogen-detectable thrombosis in the legs and pulmonary embolism. Br Med J. 1974;1:603-604.
Browse N L, Thomas M L. Source of non-lethal pulmonary emboli. Lancet. 1974;1:258-259.
Buller H R, Lensing A W A, Hirsh J, ten Cate J W. Deep venous thrombosis: new noninvasive tests. Thromb Haemost. 1991,66:133-137.
Campbell C B, Chandler J G, Tegtmeyer C J, Bernstein E F. Axillary, subclavian, and brachiocephalic vein obstruction. Surgery. 1977;82:816-826.
Cannegieter S C, Rosendaal F R, Briet E. Thromboembolic and bleeding complications in patients with mechanical heart valve prostheses. Circulation. 1994;89:635-641.
Carette S, Jobin F. Acute adrenal insufficiency as a manifestation of the anticardiolipin syndrome? Ann Rheum Dis. 1989;48:430-431.
Carter C, Gent M. The epidemiology of venous thrombosis. In Colman R, Hirsh J, Marder V, Salzman E, eds. Haemostasis and Thrombosis: Basic Principles and Clinical Practice. Philadelphia, Pa.: J B Lippincott Co; 1982:805-819.
Case records of the Massachusetts General Hospital—weekly clinicopathological exercises: case Nov. 1990, a 38-year-old woman with fever, skin lesions, thrombocytopenia, and venous thromboses. N Engl J Med. 1990,322.754-769.
Castaman G, Rodeghiero F, Dini E. Thrombotic complications during Lasparaginase treatment for acute lymphocytic leukemia. Haematologica. 1990;75.567-569.
Cheely R, McCartney W H, Perry J R, Delany D J, Bustad L, Wynia V H, Griggs T R the role of noninvasive tests versus pulmonary angiography in the diagnosis of pulmonary embolism. Am J Med 1981;70:17-22.
Chesebro J H, Fuster V, Elveback L R, McGoon D C, Pluth J R, Puga F J, Wallace R B, Danielson G K, Orszulak T A, Piehler J M, Schaff H V. Trial of combined warfarin plus dipyridamole or aspirin therapy in prosthetic heart valve replacement: danger of aspirin compared with dipyridamole. Am J Cardiol. 1983;51:1537-1541.

Chiu H M, Hirsh J, Yung W L, Regoeczi E, Gent M. Relationship between the anticoagulant and antithrombotic effects of heparin in experimental venous thrombosis. Blood. 1977,49:171-184.
Chong B H, Burgess J, Ismail F. The clinical usefulness of the platelet aggregation test for the diagnosis of heparin-induced thrombocytopenia Thromb Haemost 1993;69:344-350.
Chong B H, Fawaz I, Chesterman C N, Berndt M C. Heparin-induced thrombocytopenia mechanism of interaction of the heparin-dependent antibody with platelets. Br J Haematol. 1989;73:235-240.
Chong B H, Ismail F, Cade J, Gallus A S, Gordon S, Chesterman C N. Heparin-induced thrombocytopenia: studies with a new low molecular weight heparinoid, Org 10172. Blood. 1989;73:1592-1596.
Chong B H, Ismail F. The mechanism of heparin-induced platelet aggregation. Eur J Haematol. 1989;43:245-251.
Chong B H, Murray B, Berndt M C, Dunlop L C, Brighton T, Chesterman C N. Plasma P-selectin is increased in thrombotic consumptive platelet disorders. Blood 1994;83:1535-1541.
Chong B H, Pitney W R, Castaldi P A. Heparin-induced thrombocytopenia: association of thrombotic complications with heparin-dependent IgG antibody that induces thromboxane synthesis and platelet aggregation. Lancet. 1982;2:1246-1249.
Cines D B, Tomaski A, Tannenbaum S. Immune endothelial-cell injury in heparin-associated thrombocytopenia. N Engl J Med. 1987,316:581-589.
Cipolle R J, Rodvold K A, Seifert R, Clarens R, Ramirez-Lassepas M. Heparin-associated thrombocytopenia: a prospective evaluation of 211 patients. Ther Drug Monit. 1983;5:205-211.
Clarke C S, Otridge B W, Carney D N. Thromboembolism: a complication of weekly chemotherapy in the treatment of non-Hodgkin's lymphoma. Cancer. 1990;66 2027-2030.
Cockett F B, Thomas M L, Negus D. Iliac vein compression: its relation to iliofemoral thrombosis and the post-thrombotic syndrome. Br Med J. 1967;2.14-19.
Cogo A, Lensing A W A, Prandoni P, Hirsh J. Distribution of thrombosis in patients with deep-vein thrombosis: implications for simplifying the diagnostic process with compression ultrasound. Arch Intern Med. 1993;153:2777-2780.
Cole C W, Bormanis J. Ancrod: a practical alternative to heparin J Vasc Surg. 1988,8:59-63.
Cohen D. On the regulation and control of fibrinolysis: Edward Kowalski Memorial Lecture. Thromb Haemost. 1980;43.77-89.
Coller B S, Owen J, Jesty J, Horowitz D, Reitman M J, Spear J, Yeh T, Comp P C. Deficiency of plasma protein S, protein C, or antithrombin III and arterial thrombosis. Arteriosclerosis. 1987;7:456-462.
Collins R, Scrimgeour A, Yusuf S, Peto R. Reduction in fatal pulmonary embolism and venous thrombosis by perioperative administration of subcutaneous heparin: overview of results of randomized trials in general, orthopedic, and urologic surgery. N Engl J Med. 1988;318:1162-1173.
Comerota A J, Katz M L, Greenwald L L, Leefinans E, Czeredarczuk M, White J V. Venous duplex imaging: should it replace hemodynamic tests for deep venous thrombosis. J Vasc Surg. 1990;11:53-61.
Common H H, Seaman A J, Rosch J, Porter C T, Dotter C T. Deep vein thrombosis treated with streptokinase or heparin: follow-up of a randomized study. Angiology. 1976;27:645-654.
Conlan M G, Haire W I. Low protein S in essential thrombocythemia with thrombosis. Am J Hematol. 1989;32:88-93.
Conley C L, Rathbum U K, Monse W I II, Robinson J E Jr Circulating anticoagulant as a cause of hemorrhagic diathesis in man. Bull Johns Hopkins Hospital. 1948;83:288-296.
Conley C L. Polycythemia vera. JAMA. 1990;263:2481-2483.
Conn J W, Rovner D R, Cohen E L, Anderson J E Jr. Inhibition by heparinoid of aldosterone biosynthesis in man J Clin Endocrinol Metab. 1966,26:527-532.
Connolly S J, Laupacis A, Gent M, Roberts R S, Cairns J A, Joyner C. Canadian Atrial Fibrillation Anticoagulation (CAFA) Study. J Am Coll Cardiol. 1991;18:349-355.
Coon W W, Willis P W III, Keller J B. Venous thromboembolism and other venous disease in the Tecumseh community health study. Circulation. 1973,48;839-846.

(56) References Cited

OTHER PUBLICATIONS

Coon W W. Operative therapy of venous thromboembolism. Mod Concepts Cardiovasc Dis 1974;43:71-75.

Corrigan T P, Fossard D P, Spindler J, Armstrong P, Strachan C J, Johnston K W, Kakkar V V. Phlebography in the management of pulmonary embolism. Br J Surg 1974,61:484-488.

Cortelazzo S, Finazzi G, Ruggeri M, Vestri O, Galli M, Rodeghiero F, Barbui T Hydroxyurea for patients with essential thrombocythemia and a high risk of thrombosis. N Engl J Med 1995;332:1132-1136.

Cortelazzo S, Viero P, Finazzi G, D'Emilio A, Rodeghiero F, Barbui T. Incidence and risk factors for thrombotic complications in a historical cohort of 100 patients with essential thrombocythemia. J Clin Oncol. 1990,8:556-562.

Cronan J J, Dorfmnan G S, Scola F H, Schepps B, Alexander J. Deep venous thrombosis: US assessment using vein compression. Radiology. 1987;162:191-194.

Cronan J J, Leen V. Recurrent deep venous thrombosis: limitations of US. Radiology. 1989;170(pt 1):739-742.

Cruickshank M K, Levine M N, Hirsh J, Roberts R, Siquenza M. A standard heparin nomogram for the management of heparin therapy. Arch Intern Med. 1991;151:333-337.

Da Silva A, Widmer L K, Martin H, Mall T, Glaus L, Schneider M. Varicose veins and chronic venous insufficiency. Vasa. 1974;3:118-125.

Dahlback B, Carlsson M, Svensson P J. Familial thrombophilia due to a previously unrecognized mechanism characterized by poor anticoagulant response to activated protein C: prediction of a cofactor to activated protein C. Proc Natl Acad Sci USA. 1993;90:1004-1008.

Dahlman T, Lindvall N, Hellgren M. Osteopenia in pregnancy during long-term heparin treatment: a radiological study post partum. Br J Obstel Gynaecol. 1990;97:221-228.

Dale J, Myhre E, Loew D. Bleeding during acetylsalicylic acid and anticoagulant therapy in patients with reduced platelet reactivity after aortic valve replacement. Am Heart J. 1980;99:746-752.

Dalen J E, Alpert J S. Natural history of pulmonary embolism. Prog Cardiovasc Dis. 1975;17:259-270.

Dalen J E, Grossman W. Profiles in pulmonary embolism. In: Grossman W, ed. Cardiac Catheterization and Angiography. Philadelphia, Pa.: Lea & Febiger; 1980:336-345.

Dauzat M M, Laroche J P, Charras C, Blin B, Domingo-Faye M M, Sainte-Luce P, Domergue A, Lopez F M, Janbon C. Real-time B-mode ultrasonography for better specificity in the noninvasive diagnosis of deep venous thrombosis. J Ultrasound Med. 1986;5:625-631.

David M, Andrew M. Venous thromboembolic complications in children. J Pediatr. 1993;123:337-346.

David R, Merten D. Anderson J C, Gross S. Prevention of umbilical artery catheter clots with heparinized infusates. Dev Pharmacol Ther 1981,2:117-126.

Davies G S, Salzman E W. The pathogenesis of deep vein thrombosis. In: Joist H J, Sherman L A, eds. Venous and Arterial Thrombosis: Pathogenesis, Diagnosis, Prevention, and Therapy. New York, N Y.: Grune & Stratton; 1979:1-22.

de Swart C A M, Nijmeyer B, Roelofs J M M, Sixma J J. Kinetics of intravenously administered heparin in normal humans. Blood. 1982;60.1251-1258.

Delclos G L, Davila F. Thrombolytic therapy for pulmonary embolism in pregnancy: a case report. Am J Obstet Gynecol. 1986;155:375-376.

Demers C, Ginsberg J S, Brill-Edwards P, Panju A, Warkentin T E, Anderson D R, Turner C, Kelton J G. Rapid anticoagulation using ancrod for heparin-induced thrombocytopenia. Blood. 1991;78:2194-2197.

Demers C, Ginsberg J S. Deep venous thrombosis and pulmonary embolism in pregnancy. Clin Chest Med. 1992;13:645-656.

Derksen R H W M, de Groot P G, Kater L, Nieuwenhuis H K. Patients with antiphospholipid antibodies and venous thrombosis should receive long term anticoagulant treatment. Ann Rheum Dis. 1993;52:689-692.

Derksen R H W M, Hasselaar P, Blokzijl L, Gmelig Meyling F H, De Groot P G. Coagulation screen is more specific than the anticardiolipin antibody ELISA in defining a thrombotic subset of lupus patients. Ann Rheum Dis. 1988,47:364-371.

Deykin D, Cochios F, DeCamp G, Lopez A. Hepatic removal of activated factor X by the perfused rabbit liver. Am J Physiol. 1968;214:414-419.

Dhande V, Kattwinkel J, Alford B. Recurrent bilateral pleural effusions secondary to superior vena cava obstruction as a complication of central venous catheterization Pediatrics. 1983;72:109-113.

Donaldson G A, Williams C, Scannell J G, Shaw R G. A reappraisal of the application of the Trendelenburg operation for massive fatal embolism. N Engl J Med. 1963;268:171-174.

Donayre C E, White G H, Mehringer S M, Wilson S E. Pathogenesis determines late morbidity of axillosubelavian vein thrombosis. Am J Surg. 1986; 152:179-184.

Doyle D J, Turpie A G G, Hirsh J, Best C, Kinch D, Levine M N, Gent M. Adjusted subcutaneous heparin or continuous intravenous heparin in patients with acute deep vein thrombosis: a randomized trial. Ann Intern Med. 1987;107:441-445.

Druy E M, Trout H H III, Giordano J M, Hix W R. Lytic therapy in the treatment of axillary and subclavian vein thrombosis. J Vasc Surg. 1985;2:821-827.

Duke W. The relation of blood platelets to hemorrhagic disease: description of a method for determining the bleeding time and coagulation time and report of three cases of hemorrhagic disease relieved by transfusion. JAMA. 1910;55:1185-1192.

Dukes G E Jr, Sanders S W, Russo J Jr, Swenson E, Burnakis T G, Saffle, J R, Warden G D. Transaminase elevations in patients receiving bovine or porcine heparin. Ann Intern Med. 1984;100.646-650.

Egeberg O. Inherited antithrombin deficiency causing thrombophilia. Thromb Diath Haemorrh. 1965,13:516-530.

Elias A, Le Corff G, Bouvier J L, Benichou M, Serradimgni A. Value of real time B mode ultrasound imaging in the diagnosis of deep vein thrombosis of the lower limbs. Int Angiol. 1987;6:175-182.

Elliot M S, Immelman E J, Jeffery P, Benatar S R, Funston M R, Smith J A, Shepstone B J, Ferguson A D, Jacobs P, Walker W, Louw J H. A comparative randomized trial of heparin versus streptokinase in the treatment of acute proximal vein thrombosis an interim report of a prospective trial Br J Surg. 1979,66:838-843.

Ellison N, Beatty C P, Blake D R, Wurzel H A, MacVaugh H III. Heparin-rebound: studies in patients and volunteers. J Thorac Cardiovasc Surg. 1974;67:723-729.

Engesser L, Broekmans A W, Briet E, Brommer E J, Bertina R M. Hereditary protein S deficiency: clinical manifestations. Ann Intern Med 1987, 106 677-682.

Estelles A, Garcia-Plaza I, Dasi A, Aznar K, Duart M, Sanz G, Perez-Requejo J L, Espana F, Jimenez C, Abeledo G. Severe inherited homozygous protein C deficiency in a newborn infant. Thromb Haemost. 1984;52 53-56.

Ezekowitz M D, Bridgers S L, James K E, Carliner N H, Colling C L, Gornick C C, Krause-Steinrauf H, Kurtzke J F, Nazarian S M, Radford M J, et al. Warfarin in the prevention of stroke associated with nonrheumatic atrial fibrillation: Veterans Affairs Stroke Prevention in Nonrheumatic Atrial Fibrillation Investigators. N Engl J Med. 1992;327:1406-1412.

Favaloro E J, Bemal-Hoyos E, Exner T, Koutts J. Heparin-induced thrombocytopenia: laboratory investigation and confirmation of diagnosis. Pathology. 1992;24:177-183.

Fernandes J F, Horner J, Needham T, Nicolaides A. Ambulatory calf volume plethysmography in the assessment of venous insufficiency. Br J Surg. 1979;66:327-330.

Foley W D, Middleton W D, Lawson T L, Erickson S, Quiroz F A, Macrander S. Color Doppler ultrasound imaging of lower-extremity venous disease. AJR Am J Roentgenol. 1989;152:371-376.

Forestier F, Daffos F, Capella-Pavolvsky M. Low molecular weight heparin (PK 10169) does not cross the placenta during the second trimester of pregnancy: study by direct fetal blood sampling under ultrasound. Thromb Res. 1984,34:557-560.

Forestier F, Daffos F, Rainaut M, Toulemonde F. Low molecular weight heparin (CY 216) does not cross the placenta during the third trimester of pregnancy. Thromb Haemost. 1987,57:234. Letter.

(56) References Cited

OTHER PUBLICATIONS

Francis C W, Marder V J, Everts C M, Yaukoolbodi S. Two step warfarin therapy: prevention of postoperative venous thrombosis without excessive bleeding. JAMA. 1983;249:374-378.
Fraschini G, Jadeja J, Lawson M, Holmes F A, Carrasco H C, Wallace S. Local infusion of urokinase for the lysis of thrombosis associated with permanent central venous catheters in cancer patients. J Clin Oncol. 1987,5:672-678.
Freiman D G. The structure of thrombi. In: Colman R W, Hirsh J, Marder V J, Salzman E W, eds. Thrombosis and Hemostasis: Basic Principles and Clinical Practice. Philadelphia, Pa.: J B Lippincott; 1987:1123-1135.
Gallus A S, Goodall K T, Beswick W, Chesterman C N. Heparin-associated thrombocytopenia case report and prospective study. Aust N Z J Med. 1980;10:25-31.
Gallus A S, Hirsh J. Treatment of venous thromboembolic disease. Semin Thromb Hemost. 1976,2:291-331.
Gallus A S, Salzman E W, Hirsh J. Prevention of venous thromboembolism. In: Colman R W, Hirsh J, Marder V J, Salzman E W, eds. Haemostasis and Thrombosis: Basic Principles and Clinical Practice. 3rd ed. Philadelphia, Pa.: J B Lippincott; 1994:1331-1345.
Gallus A, Jackaman J, Tillett J, Mills W, Wycherley A. Safety and efficacy of warfarin started early after submassive venous thrombosis or pulmonary embolism. Lancet. 1986;2:1293-1296.
Gardlund B. The lupus inhibitor in thromboembolic disease and intrauterine death in the absence of systemic lupus. Acta Med Scand. 1984;215:293-298.
Gastineau D A, Kazmier F J, Nichols W L, Bowie E J. Lupus anticoagulant an analysis of the clinical and laboratory features of 219 cases. Am J Hematol 1985,19 265-275.
Gijores J E. The incidence of venous thrombosis and its sequelae in certain districts in Sweden. Acta Chir Scand. 1956;206:11-88.
Ginsberg J S, Brill-Edwards P, Burrows R F, Bona R, Prandoni P, Buller H R, Lensing A Venous thrombosis during pregnancy: leg and trimester of presentation Thromb Haemost. 1992;67:519-520.
Ginsberg J S, Hirsh J, Turner D C, Levine M N, Burrows R. Risk to the fetus of anticoagulant therapy during pregnancy. Thromb Haemost. 1989;61:197-203.
Ginsberg J S, Kowalchuk G, Hirsh J, Brill-Edwards P, Burrows R, Coates G, Webber C. Heparin effect on bone density. Thromb Haemost. 1990;64:286-289.
Ginsberg J S, Kowalchuk G, Hirsh J, Brill-Edwards P, Burrows R. Heparin therapy during pregnancy: risks to the fetus and mother. Arch Intern Med. 1989;149:2233-2236.
Ginsberg J S, Shin A, Turpie A G G, Hirsh J. Detection of previous proximal venous thrombosis with Doppler ultrasonography and photoplethysmography. Arch Intern Med. 1989;149:2255-2257.
Ginsberg J S, Wells P S, Brill-Edwards P, Donovan D, Moffatt K, Johnston M, Stevens P, Hirsh J. Antiphospholipid antibodies and venous thromboembolism. Blood. 1995;86:3685-3691.
Girolami A, Marafioti F, Rubertelli M, Cappellato M G. Congenital heterozygous plasminogen deficiency associated with a severe thrombotic tendency Acta Haematol. 1986,75.54-57.
Gissi-2. A factorial randomised trial alteplase versus streptokinase and heparin versus no heparin among 12,490 patients with acute myocardial infarction: Gruppo Italiano per lo Studio della Sopravvivenza Nell'infarto Miocardico. Lancet. 1990;336:65-71.
Gladson C L, Scharrer I, Hach V, Beck K H, Griffin J H. The frequency of type I heterozygous protein S and protein C deficiency in 141 unrelated young patients with venous thrombosis. Thromb Haemost. 1988,59:18-22.
Glazier R L, Crowell E B. Randomized prospective trial of continuous vs intermittent heparin therapy. JAMA 1976;236:1365-1367.
Glueck H I, Kant K S, Weiss M A, Pollak V E, Miller M A, Coots M. Thrombosis in systemic lupus erythematosus: relation to the presence of circulating anticoagulants. Arch Intern Med. 1985;145:1389-1395.

Goldhaber S Z, Buring J E, Lipnick R J, Hennekens C H. Pooled analyses of randomized trials of streptokinase and heparin in phlebographically documented acute deep venous thrombosis. Am J Med. 1984;76:393-397.
Gollub S. Heparin rebound in open heart surgery. Surg Gynecol Obstet. 1967;124:337-346.
Graham L Jr, Gumbiner C H. Right atrial thrombus and superior vena cava syndrome in a child. Pediatrics. 1984,73:225-229.
Green D, Lee M Y, Ito V Y, Cohn T, Press J, Filbrandt P R, VandenBerg W C, Yarkony G M, Meyer P R Jr Fixed-vs adjusted-dose heparin in the prophylaxis of thromboembolism in spinal cord injury. JAMA. 1988,260 1255-1258.
Green D, Martin G J, Shoichet S H, DeBacker N, Bomalaski J S, Lind R N. Thrombocytopenia in a prospective, randomized, double-blind trial of bovine and porcine heparin Am J Med Sci. 1984;288:60-64.
Green D. Heparin-immune thrombocytopenia. Med J Aust. 1986;144.37-39.
Green R M, Meyer T J, Dunn M, Glassroth J. Pulmonary embolism in younger adults. Chest. 1992;101:1507-1511.
Greinacher A, Amiral J, Dummel V, Vissac A, Kiefel V, Mueller-Eckhardt C Laboratory diagnosis of heparin-associated thrombocytopenia and comparison of platelet aggregation test, heparin-induced platelet activation test, and platelet factor 4/heparin enzyme-linked immunosorbent assay. Transfusion. 1994;34:381-385.
Greinacher A, Liebenhoff U, Kiefel V, Presek P, Mueller-Eckhardt C. Heparin-associated thrombocytopenia: the effects of various intravenous IgG preparations on antibody mediated platelet activation: a possible new indication for high dose i.v. IgG. Thromb Haemost. 1994;71:641-645.
Greinacher A, Michels I, Kiefel V, Mueller-Eckhardt C. A rapid and sensitive test for diagnosing heparin-associated thrombocytopenia. Thromb Haemost 1991;66:734-736.
Greinacher A, Michels I, Mueller-Eckhardt C. Heparin-associated thrombocytopenia: the antibody is not heparin specific. Thromb Haemost 1992;67:545-549.
Greinacher A, Potzsch B, Amiral J, Dummel V, Eichner A, Mueller-Eckhardt C. Heparin-associated thrombocytopenia: isolation of the antibody and characterization of a multimolecular PF4-heparin complex as the major antigen. Thromb Haemost. 1994;71:247-251.
Griffin J H Y, Evatt B, Wideman C, Fernandez J A. Anticoagulant protein C pathway defective in majority of thrombophilic patients. Blood. 1993;82:1989-1993.
Griffiths H T, Liu D T Y. Severe heparin osteoporosis in pregnancy. Postgrad Med J. 1984;60:424-425.
Grimaudo V, Gueissaz F, Hauert J, Sarraj A, Kruithof E K O, Bachmann F. Necrosis of skin induced by coumarin in a patient deficient in protein S BMJ. 1989;298:233-234.
Grollman J H Jr, Gyepes M T, Helmer E. Transfemoral selective bilateral pulmonary arteriography with a pulmonary-artery-seeking catheter. Radiology. 1970;96:202-204.
Habscheid W, Hohmann M, Wilhelm T, Epping J. Real-time ultrasound in the diagnosis of acute deep venous thrombosis of the lower extremity. Angiology 1990;41:599-608.
Haeger K. Problems of acute deep venous thrombosis, I: the interpretation of signs and symptoms. Angiology. 1969;20:219-223.
Haire W D, Lynch T G, Lieberman R P, Lund G B, Edney J A. Utility of duplex ultrasound in the diagnosis of asymptomatic catheter-induced subclavian vein thrombosis. J Ultrasound Med. 1991;10:493-496.
Hall J A G, Pauli R M, Wilson K M. Maternal and fetal sequelae of anticoagulation during pregnancy. Am J Med. 1980;68:122-140.
Hall R J, Young C, Sutton G C, Cambell S. Treatment of acute massive pulmonary embolism by streptokinase during labour and delivery. Br Med J 1972;4:647-649.
Harpel P C, Rosenberg R D. Alpha 2-macroglobulin and antithrombin-heparin cofactor: modulators of hemostatic and inflammatory reactions. Prog Hemost Thromb. 1976;3:145-189.
Harris E N, Gharavi A E, Boey M L, Patel B M, Mackworth-Young C G, Loizou S, Hughes G R. Anticardiolipin antibodies: detection by radioimmunoassay and association with thrombosis in systemic lupus erythematosus. Lancet. 1983;2:1211-1214.

(56) References Cited

OTHER PUBLICATIONS

Heckerling P S, Froelich C J, Schade S G. Retinal vein thrombosis in a patient with pernicious anemia and anticardiolipin antibodies. J Rheumatol 1989,16.1144-1146.
Heijboer H, Brandjes D P, Buller H R, Sturk A, ten Cate, J W. Deficiencies of coagulation-inhibiting and fibrinolytic proteins in outpatients with deep-vein thrombosis. N Engl J Med. 1990;323:1512-1516.
Heijboer H, Brandjes D, Lensing A W A, Buller H R, ten Cate J W. Efficacy of realtime B-mode ultrasonography versus impedance plethysmography in the diagnosis of deep vein thrombosis in symptomatic outpatients. Thromb Haemost. 1991;65:804. Abstract.
Heijboer H, Jongbloets L M M, Buller H R, Lensing A W, ten Cate J W. Clinical utility of real-time compression ultrasonography for diagnostic management of patients with recurrent venous thrombosis. Acta Radiol Scand. 1992;33:297-300.
Henny C P, ten Cate H, ten Cate J W, Prummel M F, Peters M, Buller H R. Thrombosis prophylaxis in an At III deficient pregnant woman: application of a low molecular weight heparinoid. Thromb Haemost. 1986;55:301. Letter.
Hickey W F, Garnick M B, Henderson I C, Dawson D M. Primary cerebral venous thrombosis in patients with cancer. A rarely diagnosed paraneoplastic syndrome: report of three cases and a review of the literature. Am J Med 1982,73 740-750.
Hirsh J, Dalen J E, Deykin D, Poller L. Heparin: mechanism of action, pharmacokinetics, dosing considerations, monitoring, efficacy, and safety. Chest. 1992;102(suppl 4):337S-351S.
Hirsh J, Genton E. Thrombogenesis. In: Root W S, Hoffman F G, eds. Physiological Pharmacology: A Comprehensive Treatise. New York, N.Y.: Academic Press Inc. 1974:99-133.
Hirsh J, Levine M N. Low molecular weight heparin. Blood. 1992;79:1-77.
Hirsh J, Prins M H, Samama M. Approach to the thrombophilic patient for hemostasis and thrombosis: basic principles and clinical practice. In: Colman W, Hirsh J, Marder V J, Salzman E W, eds. Hemostasis and Thrombosis: Basic Principles and Clinical Practice. 3rd ed. Philadelphia, Pa.: J B Lippincott Co; 1994:1543-1561.
Hirsh J, van Aken W G, Gallus A S, Dollery C T, Cade J F, Yung W L. Heparin kinetics in venous thrombosis and pulmonary embolism. Circulation. 1976;53:691-695.
Hirsh J. Heparin. N Engl J Med. 1991;324:1565-1574.
Hirsh J. Reliability of non-invasive tests for the diagnosis of deep vein thrombosis. Thromb Haemost. 1991;65:221-222.
Hirsh J. The optimal duration of anticoagulant therapy for venous thrombosis. N Engl J Med. 1995,332:1710-1711.
Hofmann V, Frick P G. Repeated occurrence of skin necrosis twice following coumarin intake and subsequently during decrease of vitamin K dependent coagulation factors associated with cholestasis. Thromb Haemost. 1982;48;245-246.
Holmgren K, Andersson G, Fagrell B, Johnsson H, Ljungberg B, Nilsson E, Wilhelmsson S, Zetterquist S. One-month versus six-month therapy with oral anticoagulants after symptomatic deep vein thrombosis. Acta Med Scand. 1985;218:279-284.
Hommes D W, Bura A, Mazzolai L, Buller H R, ten Cate J W. Subcutaneous heparin compared with continuous intravenous heparin administration in the initial treatment of deep vein thrombosis: a meta-analysis. Ann Intern Med. 1992;116:279-284.
Horattas M C, Wright D J, Fenton A H, Evans D M, Oddi M A, Kamienski R W, Shields E F. Changing concepts of deep venous thrombosis of the upper extremity: report of a series and review of the literature. Surgery. 1988,104:561-567.
Horellou M H, Conard J, Bertina R M, Samama M. Congenital protein C deficiency and thrombotic disease in nine French families. Br Med J (Clin Res Ed). 1984;289:1285-1287.
Horgan M J, Bartoletti A, Polansky S, Peters J C, Manning T J, Lamont B M. Effect of heparin infusates in umbilical arterial catheters on frequency of thrombotic complications. J Pediatr. 1987;111:774-778.
Huisman M V, Buller H R, ten Cate J W, Heijermans H S F, van der Laan J, van Maanen D J. Management of clinically suspected acute venous thrombosis in outpatients with serial impedance plethysmography in a community hospital setting. Arch Intern Med. 1989;149:511-513.
Huisman M V, Buller H R, ten Cate J W, Vreeken J. Serial impedance plethysmography for suspected deep vein thrombosis in outpatients. The Amsterdam General Practitioner Study. N Engl J Med. 1986;314. 823-828.
Huisman M V, Buller H R, ten Cate J W. Utility of impedance plethysmography in the diagnosis of recurrent deep-vein thrombosis. Arch Intern Med. 1988;148:681-683.
Hull R D, Carter C J, Jay R M, Ockelford P A, Hirsh J, Turpie A G G, Zielinsky A, Gent M, Powers P J. The diagnosis of acute, recurrent, deep-vein thrombosis: a diagnostic challenge. Circulation, 1983;67:901-906.
Hull R D, Hirsh J, Carter C J, Jay R M, Dodd P E, Ockelford P A, Coates G, Gill G J, Turpie A G G, Doyle D J, Buller H R, Raskob G E. Pulmonary angiography, ventilation lung scanning, and venography for clinically suspected pulmonary embolism with abnormal perfusion lung scan. Ann Intern Med. 1983,98:891-899.
Hull R D, Hirsh J, Carter C J, Jay R M, Ockelford P A, Buller H R, Turpie A G G, Powers P, Kinch D, Dodd P E, Gill G J, Leclerc J R, Gent M. Diagnostic efficacy of impedance plethysmography for clinically suspected deep-vein thrombosis: a randomized trial. Ann Intern Med. 1985;102:21-28.
Hull R D, Hirsh J, Carter C J, Raskob G E, Gill G J, Jay R M, Leclerc J R, David M, Coates G. Diagnostic value of ventilation-perfusion lung scanning in patients with suspected pulmonary embolism. Chest. 1985;88:819-828.
Hull R D, Hirsh J, Sackett D L, Taylor D W, Carter C, Turpie A G G, Powers P, Gent M. Clinical validity of a negative venogram in patients with clinically suspected venous thrombosis. Circulation. 1981;64:622-625.
Hull R D, Raskob G E, Carter C J, Coates G, Gill G J, Sackett D L, Hirsh J, Thompson M. Pulmonary embolism in outpatients with pleuritic chest pain. Arch Intern Med. 1988,148:838-844.
Hull R D, Raskob G E, Carter C J. Serial impedance plethysmography in pregnant patients with clinically suspected deep-vein thrombosis: clinical validity of negative findings. Ann Intern Med. 1990;112:663-667.
Hull R D, Raskob G E, Coates G, Panju A A. Clinical validity of a normal perfusion lung scan in patients with suspected pulmonary embolism. Chest. 1990;97:23-26.
Hull R D, Raskob G E, Hirsh J, Jay R M, Leclerc J R, Geerts W H, Rosenbloom D, Sackett D L, Anderson C, Harrison L, Gent M. Continuous intravenous heparin compared with intermittent subcutaneous heparin in the initial treatment of proximal-vein thrombosis. N Engl J Med. 1986;315:1109-1114.
Hull R D, Raskob G E, LeClerc J R, Jay R M, Hirsh J. The diagnosis of clinically suspected venous thrombosis. Clin Chest Med. 1984;5:439-456.
Hull R D, Raskob G E, Pineo G, Rosenbloom D, Evans W, Mallory T, Anquist K, Smith F, Hughes G, Green D, Elliott G, Panju A, Brant R. A comparison of subcutaneous low-molecular-weight heparin with warfarin sodium for prophylaxis against deep-vein thrombosis after hip or knee implantation. N Engl J Med. 1993;329:1370-1376.
Hull R D, Raskob G E, Rosenbloom D, Panju A A, Brill-Edwads P, Ginsberg J S, Hirsh J, Martin G J, Green D. Heparin for 5 days as compared with 10 days in the initial treatment of proximal venous thrombosis. N Engl J Med 1990;322:1260-1264.
Hull R, Delmore T J, Hirsh J, Gent M, Armstrong P, Lofthouse R, MacMillan A, Blackstone I, Reed-Davis R, Detwiler R C. Effectiveness of intermittent pulsatile elastic stockings for the prevention of calf and thigh vein thrombosis in patients undergoing elective knee surgery. Thromb Res. 1979,16:37-45.
Hull R, Delmore T, Carter C, Hirsh J, Genton E, Gent M, Turpie A G G, McLoughlin D. Adjusted subcutaneous heparin vs warfarin sodium in the long-term treatment of venous thrombosis. N Engl J Med. 1982;306: 189-194.
Hull R, Delmore T, Genton E, Hirsh J, Gent M, Sackett D, McLoughlin D, Armstrong P. Warfarin sodium versus low-dose heparin in the long-term treatment of venous thrombosis. N Engl J Med. 1979;301:855-858.

(56) References Cited

OTHER PUBLICATIONS

Hull R, Hirsh J, Jay R M, Carter C, England C, Gent M, Turpie A G G, McLoughlin D, Dodd P, Thomas M, Raskob G, Ockelford P. Different intensities of oral anticoagulant therapy in the treatment of proximal-vein thrombosis. N Engl J Med. 1982;307:1676-1681.

Hull R, van Aken W G, Hirsh J, Gallus A S, Hoicka G, Turpie A G G, Walker I, Gent M. Impedance plethysmography using the occlusive cuff technique in the diagnosis of venous thrombosis. Circulation. 1976;53:696-700.

Hume M, Sevitt S, Thomas D P Mechanisms of venous thromboembolism in Hume M, Sevitt S, Thomas D P, eds. Venous Thrombosis and Pulmonary Embolism. Cambridge, Mass: Harvard University Press; 1970:85-114.

Hunter J A, DeLaria G A, Goldin M D, Serry C, Monson D O, DaValle M J, Najafi H. Inferior vena cava interruption with the Hunter-Sessions balloon: eighteen years' experience in 191 cases. J Vasc Surg. 1989;10:450-456.

Hunter J A, Sessions R, Petasnick J. Therapeutic balloon occlusion of the inferior vena cava. JAMA. 1975,234:1034-1037.

ISIS-3: a randomised comparison of streptokinase vs tissue plasminogen activator vs anistreplase and of aspirin plus heparin vs aspirin alone among 41,299 cases of suspected acute myocardial infarction. Lancet. 1992;339:753-770.

Iturbe-Alessio I, Fonseca M C, Mutchinik O, Santos M A, Zajarias A, Salazar E. Risks of anticoagulant therapy in pregnancy women with artificial heart valves. N Engl J Med. 1986;315:1390-1393.

Jabaily J, Iland H J, Laszlo J, Massey E W, Faguet G B, Briere J, Landaw S A, Pisciotta A V. Neurologic manifestations of essential thrombocythemia. Ann Intern Med. 1983,99:513-518.

James W I. Trousseau's syndrome. Int J Dermatol. 1984;23:205-206.

Jay R, Hull R, Carter C, Ockelford P, Buller H, Turpie A G G, Hirsh J. Outcome of abnormal impedance plethysmography results in patients with proximal-vein thrombosis: frequency of return to normal. Thromb Res. 1984,36:259-263.

Johnston K W, Kakkar V V. Plethysmographic diagnosis of deep vein thrombosis. Surg Gynecol Obstet. 1974;139:41-44.

Jones T K, Barnes R W, Greenfield L J Greenfield vena caval filter: rationale and current indications. Ann Thorac Surg. 1986;42(suppl):S48-S55.

Kakkar V V, Howe C T, Flanc C, Clarke M B. Natural history of postoperative deep vein thrombosis. Lancet. 1969;2 230-232.

Kakkar V V, Howe C T, Nicolaides A N, Renney J T, Clarke M B. Deep vein thrombosis of the leg: is there a high risk group? Am J Surg. 1970;120.527-530.

Kapsch D N, Adelstein E H, Rhodes G R, Silver D. Heparin-induced thrombocytopenia, thrombosis, and hemorrhage. Surgery 1979,86:148-155.

Kaunitz A M, Hughes J M, Grimes D A, Smith J C, Rochat R W, Kafrissen M E. Causes of maternal mortality in the United States. Obstet Gynecol. 1985;65 605-612.

Kelton J G, Sheridan D, Brain H, Powers P J, Turpie A G G, Carter C J. Clinical usefulness of testing for a heparin-dependent platelet-aggregating factor in patients with suspected heparin-associated thrombocytopenia. J Lab Clin Med 1984;103:606-612.

Kelton J G, Sheridan D, Santos A, Smith J, Steeves K, Smith C, Brown C, Murphy W G. Heparin-induced thrombocytopenia: laboratory studies. Blood 1988;72:925-930.

Kelton J G, Smith J W, Warkentin T E, Hayward C P M, Denomme G A, Horsewood P. Immunoglobulin G from patients with heparin-induced thrombocytopenia binds to a complex of heparin and platelet factor 4. Blood. 1994;83:3232-3239.

Khamashta M A, Cuadrado M J, Mujic F, Taub N A, Hunt B J, Hughes G R V. The management of thrombosis in the antiphospholipid-antibo-dy syndrome. N Engl J Med. 1995;332:993-997.

King D J, Kelton J G. Heparin-associated thrombocytopenia. Ann Intern Med. 1984;100:535-540.

Kipper M S, Moser K M, Kortman K E, Ashburn W L. Longterm follow-up of patients with suspected pulmonary embolism and a normal lung scan: perfusion scans in embolic suspects. Chest. 1982;82:411-415.

Kisiel W, Canfield W M, Ericsson L H, Davie E W. Anticoagulant properties of bovine plasma protein C following activation by thrombin. Biochemistry. 1977;16:5824-5831.

Kitchens C S. Prolonged activated partial thromboplastin time of unknown etiology: a prospective study of 100 consecutive cases referred for consultation. Am J Hematol. 1988;27:38-45.

Kleinsasser L J. "Effort" thrombosis of the axillary and subclavian veins. Arch Surg. 1949;59:258.

Kneeland J B, Auh Y H, Zirinsky K, Rubenstein W, Kazam E. MR, CT, and ultrasonographic demonstration of splenic vein thrombosis. J Comput Assist Tomogr. 1984;8:1199-1200.

Koster T, Rosendaal F R, de Ronde H, Briet E, Vandenbroucke J P, Bertina R M. Venous thrombosis due to poor anticoagulant response to activated protein C: Leiden Thrombophilia Study. Lancet. 1993;342:1503-1506.

Kramer S S, Taylor G A, Garfinkel D J, Simmons M A. Lethal chylothoraces due to superior vena caval thrombosis in infants. AJR Am J Roentgenol. 1981;137:559-563.

Krishnamurti C, Bolan C D, Reid T J III, Alving B M. Pharmacology and mechanism of action of ancrod: potential for inducing thrombosis. Blood. 1992,79:2492. Letter.

Lagerstedt C I, Olsson C G, Fagher B O, Oqvist B W, Albrechtsson U. Need for long-term anticoagulant treatment in symptomatic calf-vein thrombosis. Lancet. 1985;2:515-518.

Landefeld C S, Goldman L. Major bleeding in outpatients treated with warfarin: incidence and prediction by factors known at the start of outpatient therapy. Am J Med. 1989;87:144-152.

Landefeld C S, Rosenblatt M W, Goldman L. Bleeding in outpatients treated with warfarin: relation to the prothrombin time and important remediable lesions. Am J Med. 1989;87:153-159.

Lansing A M, Davis W M. Five-year follow-up study of iliofemoral venous thrombectomy. Ann Surg. 1968; 168:620-628.

Le Coultre C, Oberhansli I, Mossaz A, Bugmann P, Faidutti B, Belli D C. Postoperative chylothorax in children: differences between vascular and traumatic origin. J Pediatr Surg. 1991;26:519-523.

Le D T, Griffin J H, Greengard J S, Mujumdar V, Rapaport S I. Use of a generally applicable tissue factor-dependent factor V assay to detect activated protein C-resistant factor Va in patients receiving warfarin and in patients with a lupus anticoagulant. Blood. 1995,85:1704-1711.

Lechner K, Pabinger-Fasching I. Lupus anticoagulants and thrombosis a study of 25 cases and review of the literature. Haemostasis. 1985;15:254-262.

Lee L. Reticuloendothelial clearance of circulating fibrin in the pathogenesis of the generalized Shwartzman reaction. J Exp Med. 1962;115:1065-1082.

Leehey D, Gantt C, Lim V. Heparin-induced hypoaldosteronism report of a case. JAMA. 1981;246:2189-2190.

Lensing A W A, Buller H R, Prandoni P, Batchelor D, Molenaar A H, Cogo A, Vigo M, Huisman P M, ten Cate J W. Contrast venography, the gold standard for the diagnosis of deep-vein thrombosis: improvement in observer agreement. Thromb Haemost. 1992,67.8-12.

Lensing A W A, Hirsh J. Rationale and results of thrombolytic therapy for deep vein thrombosis. In: Bernstein E F, ed. Vascular Diagniosis. St Louis, Mo.: Mosby-Year Book, Inc. 1993:875-879.

Lensing A W A, Prandoni P, Brandjes D, Huisman P M, Vigo M, Tomasella A, Krekt J, ten Cate J W, Huisman M V, Buller H R. Detection of deep-vein thrombosis by real-time B-mode ultrasonography. N Engl J Med. 1989;320.342-345.

Levine M N, Hirsh J, Gent M, Turpie A G G, Cruickshank M, Weitz J, Anderson D, Johnston M. A randomized trial comparing the activated thromboplastin time with heparin assay in patients with acute venous thromboembolism requiring large daily doses of heparin. Arch Intern Med. 1994;154:49-56.

Levine M N, Hirsh J, Gent M, Turpie A G G, Weitz J, Ginsberg J, Geerts W, Leclerc J, Neemeh J, Powers P, Piovella F. Optimal duration of oral anticoagulant therapy: a randomized trial comparing four weeks with three months of warfarin in patients with proximal deep vein thrombosis. Thromb Haemost. 1995,74:606-611.

Levine M N, Hirsh J, Kelton J G. Heparin-induced bleeding. In Lane D A, Lindahl U, eds. Heparini: Chemical and Biological Properties, Clinical Applications. London, UK: Edward Arnold; 1989:517-532.

(56) References Cited

OTHER PUBLICATIONS

Levine M N, Hirsh J, Landefeld S, Raskob G. Hemorrhagic complications of anticoagulant treatment. Chest. 1992;102(suppl):352S-363-S.
Levine M N, Raskob G, Hirsh J. Hemorrhagic complications of long-term anticoagulant therapy. Chest. 1989;95(suppl):26S-36S.
Levine MN, Gent M, Hirsh J, Arnold A, Goodyear M D, Hryniuk W, De Pauw S. The thrombogenic effect of anticancer drug therapy in women with stage II breast cancer. N Engl J Med. 1988;318:404-407.
Levine S R, Kieran S, Puzio K, Feit H, Patel S C, Welch K M. Cerebral venous thrombosis with lupus anticoagulants: report of two cases. Stroke. 1987;18:801-804.
Leyvraz P F, Bachmann F, Hoek J, Buller H R, Postel M, Samama M. Prevention of deep vein thrombosis after hip replacement: randomised comparison between unfractionated heparin and low molecular weight heparin. BMJ. 1991;303:543-548.
Leyvraz P F, Richard J, Bachmann F, Van Melle G, Treyvaud J M, Livio J J, Candardjis G. Adjusted versus fixed-dose subcutaneous heparin in the prevention of deep-vein thrombosis after total hip replacement. N Engl J Med. 1983;309:954-958.
Li J -M, Anderson F A, Wheeler H B. Noninvasive testing for venous reflux using photoplethysmography: standardization of technique and evaluation of interpretation criteria. Bruit. 1983;7:25.
Lindblad B, Bergqvist D. Aggressive or conservative treatment in subclavian vein thrombosis. In: Eklof B, Gjores J, Thulesius O, Bergqvist D, eds. Controversies in the Management of Venous Disorders: Scandinavian Contributions on Venoits Problems With Comments by International Authorities. London, UK: Butterworths; 1989:141-158.
Lindblad B, Bornmyr S, Kullendorff B, Bergqvist D. Venous haemodynamics of the upper extremity after subclavian vein thrombosis. Vasa. 1990;19:218-222.
Lindblad B, Tengborn L, Bergqvist D. Deep vein thrombosis of the axillary-subclavian veins: epidemiologic data, effects of different types of treatment and late sequelae. Eur J Vasc Surg. 1988;2:161-165.
Liu P G, Jacobs J B, Reede D. Trousseau's syndrome in the head and neck Am J Otolaryngol. 1985,6:405-408.
Lockshin M D. Antiphospholipid antibody syndrome. JAMA. 1992,268:1451-1453.
Love P E, Santoro S A. Antiphospholipid antibodies: anticardiolipin and the lupus anticoagulant in systemic lupus erythematosus (SLE) and in non-SLE disorders: prevalence and clinical significance. Ann Intern Med. 1990;112:682-698.
Machieder H I. Evaluation of a new treatment strategy for Paget-Schroetter syndrome: spontaneous thrombosis of the axillary-subclavian vein. J Vasc Surg. 1993;17:305-315.
Machleder H I. The role of thrombolytic agents for acute subclavian vein thrombosis. Semin Vasc Surg. 1992;5:82.
Mackworth-Young C G, Loizou S, Walport M J. Primary antiphospholipid syndrome: features of patients with raised anticardiolipin antibodies and no other disorder. Ann Rheum Dis. 1989;48:362-367.
Magnani H N. Heparin-induced thrombocytopenia (HIT): an overview of 230 patients treated with orgaran (Org 10172). Thromb Haemost. 1993;70:554-561.
Magnant J G, Walsh D B, Juravsky L I, Cronenwett J L. Current use of inferior vena cava filters. J Vasc Surg. 1992;16:701-706.
Mannucci P M, Tripodi A, Bertina R M. Protein S deficiency associated with juvenile arterial and venous thromboses. Thromb Haemost. 1986,55:440. Letter.
Marciniak E, Wilson H D, Marlar R A Neonatal purpura fliminans: a genetic disorder related to the absence of protein C in blood. Blood. 1985;65:15-20.
Marlar R A, Kleiss A J, Griffin J H. Human protein C: inactivation of factors V and VIII in plasma by the activated molecule. Ann N Y Acad Sci. 1981;370:303-310.
Martin E C, Koser M, Gordon D H. Venography in axillary-subclavian vein thrombosis. Cardiovasc Radiol. 1979;2:261-266.

Mattos M A, Londrey G L, Leutz D W, Hodgson K J, Ramsey D E, Barkmeier L D, Stauffer E S, Spadone D P, Sumner D S. Color-flow duplex scanning for the surveillance and diagnosis of acute deep venous thrombosis. J Vasc Surg. 1992;15:366-375.
McIntyre K J, Hoagland H C, Silverstein M N, Petitt R M. Essential thrombocythemia in young adults. Mayo Clin Proc. 1991;66:149-154.
McKenna R, Cole E R, Vasan U. Is warfarin sodium contraindicated in the lactating mother? J Pediatr. 1983;103:325-327.
McLachlin J, Richards T, Paterson J C. An evaluation of clinical signs in the diagnosis of venous thrombosis. Arch Surg. 1962;85:738-744.
McNamara T O, Fischer J R. Thrombolysis of peripheral arterial and graft occlusions: improved results using high-dose urokinase. AJR Am J Roentgenol. 1985;144:769-775.
McNeil B J Ventilation-perfusion studies and the diagnosis of pulmonary embolism: concise communication. J Nucl Med. 1980;21:319-323.
Melissari E, Das S, Kanthou C, Pemberton K D, Kakkar V V. The use of LMW heparin in treating thromboembolism during pregnancy and prevention of osteoporosis. Thromb Haemost. 1991;65:926. Abstract.
Meyerovitz M F, Levin D C, Harrington D P, Boxt L M, Bettmann M A, Garnic J D, Barry W H, Geller S C. Evaluation of optimized biplane pulmonary cineangiography. Invest Radiol. 1985;20:945-949.
Miller G A H, Hall R J C, Paneth M. Pulmonary embolectomy, heparin, and streptokinase: their place in the treatment of acute massive pulmonary embolism. Am Heart J. 1977;93:568-574.
Miller G A H, Sutton G C, Kerr I H, Gibson R V, Honey M. Comparison of streptokinase and heparin in the treatment of isolated acute massive pulmonary embolism. Br Med J 1971;2:681-684.
Mintz G, Acevedo-Vazquez E, Gutierrez-Espinosa G, Avelar-Garnica F. Renal vein thrombosis and inferior vena cava thrombosis in systemic lupus erythematosusfrequency and risk factors. Arthritis Rheum. 1984,27:539-544.
Mobin-Uddin K, Callard G M, Bolooki H, Rubinson MichieD D, Jude Jr. Transvenous caval interruption with an umbrella filter. N Engl J Med. 1972.286:55-58.
Mobin-Uddin K. The intracaval umbrella in prevention of pulmonary embolism. In: Bergan J J, Yao J S T, eds. Vetious Problems. Chicago, Ill.: Year Book Medical Publishers Inc; 1978:333-346.
Mollitt D L, Golladay E S. Complications of TPN catheter-induced vena caval thrombosis in children less than one year of age. J Pediatr Surg. 1983;18:462-467.
Monreal M, Lafoz E, Olive A, del Rio L, Vedia C. Comparison of subcutaneous unfractionated heparin with a low molecular weight heparin (Fragmin) in patients with venous thromboembolism and contraindications to coumarin. Thromb Haemost. 1994;71:7-11.
Monreal M, Lafoz E, Ruiz J, Valls R, Alastrue A. Upper-extremity deep venous thrombosis and pulmonary embolism: a prospective study. Chest. 1991;99:280-283.
Monreal M, Montserrat E, Salvador R, Bechini J, Donoso L, MaCallejas J, Foz M. Real-time ultrasound for diagnosis of symptomatic venous thrombosis and for screening of patients at risk: correlation with ascending conventional venography. Angiology. 1989;40:527-533.
Moreb J, Kitchens C S. Acquired functional protein S deficiency, cerebral venous thrombosis, and coumarin skin necrosis in association with antiphospholipid syndrome: report of two cases. Am J Med. 1989;87:207-210.
Moschos C B, Khan M I, Regan T J. Thrombogenic properties of blood during early ischemic and nonischemic injury Am J Physiol. 1971,220:1882-1884.
Moser K M, Auger W R, Fedullo P F. Chronic major-vessel thromboembolic pulmonary hypertension. Circulation. 1990;81:1735-1743.
Moser K M, Daily P O, Peterson K, Dembitsky W, Vapnek J M, Shure D, Utley J, Archibald C. Thromboendarterectomy for chronic, major-vessel thromboembolic pulmonary hypertension: immediate and long-term results in 42 patients. Ann Intern Med. 1987;107:560-565.

(56) References Cited

OTHER PUBLICATIONS

Moser K M, Harsany P G, Harvey-Smith W, Durante P L, Guisan M. Reversible interruption of inferior vena cava by means of a balloon catheter: preliminary report. J Thorac Cardiovasc Surg. 1971;62:205-212.

Mulvihill S J, Fonkalsrud E W. Complications of superior versus inferior vena cava occlusion in infants receiving central total parenteral nutrition. J Pediatr Surg. 1984;19:752-757.

Negus D. The post-thrombotic syndrome. Am R Coll Surg Engl. 1970;47:92-105.

Nelson J C, Lerner R G, Goldstein R, Cagin N A. Heparin-induced thrombocytopenia. Arch Intern Med. 1978;138:548-552.

Nicolaides A N, Kakkar V V, Field E S, Renney J T. The origin of deep vein thrombosis: a venographic study. Br J Radiol. 1971;44:653-663.

Norman C S, Proven J L. Control and complications of intermittent heparin therapy. Surg Gynecol Obstet. 1977;145.338-342.

Novelline R A, Baltarowich O H, Athanasoulis C A, Waltman A C, Greenfield A J, McKusick K A. The clinical course of patients with suspected pulmonary embolism and a negative pulmonary arteriogram. Radiology. 1978;126:561-567.

O'Donnell T F, Browse N L, Burnand K G, et al. The socioeconomic effects of iliofemoral venous thrombosis. J Surg Res. 1977,22:483-488.

Olsson P, Lagergren H, Ek S. The elimination from plasma of intravenous heparin: an experimental study on dogs and humans. Acta Med Scand 1963;173:619-630.

Omri A, Delaloye J F, Andersen H, Bachmann F. Low molecular weight heparin Novo (LHN-1) does not cross the placenta during the second trimester of pregnancy. Thromb Haeniost. 1989;61:55-56.

Optimum duration of anticoagulation for deep-vein thrombosis and pulmonary embolism. Lancet. 1992;340:873-876.

Orme M L, Lewis P J, de Swiet M, Serlin M J, Sibeon R, Baty J D, Breckenridge A M. May mothers given warfarin breast-feed their infants? Br Med J 1977;1:1564-1565.

Ostermiller W Jr, Carter R. Mesenteric venous thrombosis secondary to polycythemia vera. Am Surg. 1969;35:407-409.

O'Sullivan E F. Duration of anticoagulant therapy in venous thromboembolism. Med J Aust. 1972;2:1104-1107.

Pabinger-Fasching I, Deutsch E. Protein C deficiency in Austria. Semin Thromb Hemost. 1985;11:347-351.

Painter T D, Karpf M. Deep venous thrombosis of the upper extremity five years' experience at a university hospital. Anigiology. 1984,35:743-749.

Persson A V, Jones C, Zide R, Jewell E R Use of the triex scanner in diagnosis of deep venous thrombosis. Arch Surg. 1989,124 593-596.

Pertuiset E, Tribout B, Wechsler B, Bellin M F, Godeau P, Jian R, Rambaud J C. Systemic lupus erythematosus presenting with portal venous thrombosis. Am J Med. 1989;86:501-502.

Peters S H A, Jonker J J C, de Boer A C, den Ottolander G J. Home-diagnosis of deep venous thrombosis with impedance plethysmography. Thromb Haemost. 1982;48:297-300.

Petersen P, Boysen G, Godttredsen J, Andersen E I D, Andersen, B. Placebo-controlled, randomised trial of warfarin and aspirin for prevention of thromboembolic complications in chronic atrial fibrillation: the Copenhagen AFASAK Study. Lancet. 1989;1:175-179.

Phelps K R, Oh M S, Carroll R I. Heparin-induced hyperkalemia: report of a case. Nephron. 1980,25:254-258.

Pifarre R, Sullivan H J, Montoya A, Bakhos M, Grieco J, Foy B K B, Blakeman B. Management of blood loss and heparin rebound following cardiopulmonary bypass. Semin Thromb Hemost. 1989;15:173-177.

Pini M, Pattachini C, Quintavalla R, Poli T, Megha A, Tagliaferri A, Manotti C, Dettori A G. Subcutaneous vs intravenous heparin in the treatment of deep venous thrombosis: a randomized clinical trial. Thromb Haemost. 1990;64:222-226.

Pitney W R, Holt P J, Bray C, Bolton G. Acquired resistance to treatment with arvin. Lancet. 1969,1:79-81.

Plate G, Ohlin P, Eklof B. Pulmonary embolism in acute iliofemoral venous thrombosis. Br J Surg 1985,72,912-915.

Pope J M, Canny C L B, Bell D A. Cerebral ischemic events associated with endocarditis, retinal vascular disease, and lupus anticoagulant. Am J Med. 1991,90:299-309.

Powers P J, Cuthbert D, Hirsh J. Thrombocytopenia found uncommonly during heparin therapy JAMA. 1979;241:2396-2397.

Powers P J, Gent M, Jay R M, Julian D H, Turpie A G G, Levine M, Hirsh J. A randomized trial of less intense postoperative warfarin or aspirin therapy in the prevention of venous thromboembolism after surgery for fractured hip. Arch Intern Med. 1989;149:771-774.

Powers P J, Kelton J G, Carter C J. Studies on the frequency of heparin-associated thrombocytopenia. Thromb Res. 1984,33:439-443.

Prandoni P, Cogo A, Bernardi E, Villalta S, Polistena P, Simioni P, Noventa F, Benedetti L, Girolami A. A simple ultrasound approach for detection of recurrent proximal-vein thrombosis. Circulatiom. 1993;88(pt 1):1730-1735.

Prandoni P, Lensing A W A, Buller F R, Cogo A, Prins M H, Cattelan A M, Cuppini S, Noventa F, ten Cate J W. Deep-vein thrombosis and the incidence of subsequent symptomatic cancer. N Engl J Med. 1992;327:1128-1133.

Prandoni P, Lensing A W A, Buller H R, Carta M, Cogo A, Vigo A M, Casara D, Ruol A, ten Cate J W. Comparison of subcutaneous low-molecular-weight heparin with intravenous standard heparin in proximal deep-vein thrombosis. Lancet. 1992;339:441-445.

Prandoni P, Lensing A W A, Buller H R, Carta M, Vigo M, Cogo A, Cuppini S, ten Cate J W. Failure of computerized impedance plethsmography in the diagnostic management of patients with clinically suspected deep vein thrombosis. Thromb Haemost. 1991,65:233-236.

Prandoni P, Lensing A W A, Buller H R, Cogo A, Prins M H, Cattelan A M, Cuppini S, Noventa F, ten Cate J W. Deep-vein thrombosis and the incidence of subsequent symptomatic cancer. N Engl J Med. 1992;327:1128-1133.

Prandoni P, Lensing A W A, Carta M, Cogo A, Villalta S, Ruol A. Elastic compression stockings and the postphlebitic syndrome: an interim analysis of a prospective cohort study in patients with proximal vein thrombosis. Thromb Haemost. 1991;65:1579. Abstract.

Prandoni P, Lensing A W A, Cogo A, Cuppini S, Villalta S, Carta M, Cattelan A M, Polistena P, Bernardi E, Prins M H. The long-term clinical course of acute deep-vein thrombosis. Ann Intern Med. In press.

Preliminary report of the Stroke Prevention in Atrial Fibrillation Study. N Engl J Med. 1990,322:863-868.

Prins N I H, Hirsh J. A critical review of the evidence supporting a relationship between impaired fibrinolytic activity and venous thromboembolism. Arch Intern Med. 1991;151:1721-1731.

Priollet P, Roncato M, Aiach M, Housset E, Poissonnier M H, Chavinie J. Low-molecular-weight heparin in venous thrombosis during pregnancy. Br J Haematol. 1986;63 605-606.

Rabinov K, Paulin S. Roentgen diagnosis of venous thrombosis in the leg. Arch Surg. 1972;104:134-144.

Racanelli A, Fareed J, Walenga JM, Coyne E. Biochemical and pharmacologic studies on the protamine interactions with heparin, its fractions and fragments. Semin Thromb Hemost. 1985;11:176-189.

Raghavendra B N, Rosen R J, Lam S, Riles T, Horii S C. Deep venous thrombosis: detection by high-resolution real-time ultrasonography. Radiology. 1984;152:789-793.

Rajani K, Goetzman B W, Wennberg R P, Turner E, Abildgaard C. Effect of heparinization of fluids infused through an umbilical artery catheter on catheter patency and frequency of complications. Pediatrics. 1979;63:552-556.

Ramirez-Lassepas M, Cipolle R J, Rodvold K A, Seifert R D, Strand L, Taddeini L, Cusulos M. Heparin-induced thrombocytopenia in patients with cerebrovascular ischemic disease. Neurology. 1984;34:736-740.

Rao A K, White G C, Shermnan L, Colman R, Lan G, Ball A P Low incidence of thrombocytopenia with porcine mucosal heparin: a prospective multicenter study. Arch Intern Med. 1989,149:1285-1288.

Rao R H, Vagnucci A H, Amico J A. Bilateral massive adrenal hemorrhage: early recognition and treatment. Ann Intern Med. 1989;110:227-235.

(56) References Cited

OTHER PUBLICATIONS

Raschke R A, Reilly B M, Guidry J R, Fontana J R, Srinivas S. The weight-based heparin dosing nomogram compared with a standard care nomogram: a randomized controlled trial. Ann Intern Med. 1993;119:874-881.
Risk factors for stroke and efficacy of antithrombotic therapy in atrial fibrillation: analysis of pooled data from five randomized controlled trials. Arch Intern Med. 1994;154:1449-1457.
Rockoff M A, Gang D L, Vacanti J P. Fatal pulmonary embolism following removal of a central venous catheter. J Pediatr Surg. 1984;19:307-309.
Rodgers G M. Activated protein C resistance and inherited thrombosis. Am J Clin Pathol. 1995;103:261-262.
Roehm J O Jr. The bird's nest filter: a new percutaneous transcatheter inferior vena cava filter. J Vasc Surg. 1984;1:498-501.
Rose S C, Zwiebel W J, Nelson B D, Priest D L, Knighton R A, Brown J W, Lawrence P F, Stults B M, Reading J C, Miller F J. Symptomatic lower extremity deep venous thrombosis: accuracy, limitations, and role of color duplex flow imaging in diagnosis. Radiology. 1990;175:639-644.
Rosenberg R D. Hypercoagulability and methods for monitoring anticoagulant therapy. In: Fratantoni J, Wessler S, eds. Prophylactic Therapy of Deep Vein Thrombosis and Pulmonary Embolism Proceedings of a Conference. Bethesda, Md.: National Institutes of Health; 1975. US Dept of Health, Education, and Welfare Publication NIH 76-866.
Rubenstein M, Creger W P. Successful streptokinase therapy for catheter-induced subclavian vein thrombosis. Arch Intern Med. 1980;140:1370-1371.
Rubinstein I, Murray D, Hoffstein V. Fatal pulmonary emboli in hospitalized patients: an autopsy study. Arch Intern Med. 1988,148: 1425-1426.
Sack G H Jr, Levin J, Bell W R. Trousseau's syndrome and other manifestations of chronic disseminated coagulopathy in patients with neoplasms clinical, pathophysiologic and therapeutic features. Medicine (Baltimore) 1977,56:1-37.
Salzman E W, Davies G C. Prophylaxis of venous thromboembolism: analysis of cost effectiveness. Ann Surg. 1980,191:207-218.
Salzman E W, Deykin D, Shapiro R M, Rosenberg R. Management of heparin therapy: controlled prospective trial. N Engl J Med. 1975;292:1046-1050.
Salzman E W, Rosenberg R D, Smith M N, Lindon J N, Favreau L Effect of heparin and heparin fractions on platelet aggregation. J Clin Invest 1980,65:64-73.
Samama M, Horellou M H, Soria J, Conard J, Nicolas G. Successful progressive anticoagulation in a severe protein C deficiency and previous skin necrosis at the initiation of oral anticoagulation treatment. Thromb Haemost. 1984,51:132-133. Letter.
Saour J N, Sieck J O, Mamo L A R, Gallus A S. Trial of different intensities of anticoagulation in patients with prosthetic heart valves. N Engl J Med. 1990;322:428-432.
Schindler J M, Kaiser M, Gerber A, Vuilliomenet A, Popovic A, Bertel O. Colour coded duplex sonography in suspected deep vein thrombosis of the leg. BMJ. 1990,301.1369-1370.
Schmidt B, Andrew A. A prospective international registry of neonatal thrombotic diseases. Pediatr Res. 1994;35(pt 2) 170a. Abstract.
Schroeder T M, Elkins R C, Greenfield L J. Entrapment of sized emboli by the KMA-Greenfield intracaval filter. Surgery. 1978;83:435-439.
Schulman S, Lockner D, Juhlin-Dannfelt A. The duration of oral anticoagulation after deep vein thrombosis: a randomized study. Acta Med Scand. 1985;217:547-552.
Schulman S, Rhedin A S, Lindmarker P, Carlsson A, Lators G, Nicol P, Loogna E, Svensson E, Ljungberg B, Walter H, et al. A comparison of six weeks with six months of oral anticoagulation after a first episode of venous thromboembolism: Duration of Anticoagulation Trial Study Group. N Engl J Med. 1995;332:1661-1665.
Sethi G K, Copeland J G, Goldman S, Moritz T, Zadina K, Henderson W G. Implications of preoperative administration of aspirin in patients undergoing coronary artery bypass grafting: Department of Veterans Affairs Cooperative Study on Antiplatelet Therapy. J Am Coll Cardiol. 1990;15:15-20.
Shaldon S, Sherlock L. Portal hypertension in the myeoloproliferative syndrome and the reticuloses. Am J Med 1962;32:758-764.
Shapira N, Schaff H V, Piehler J M, White R D, Still J C, Pluth J R. Cardiovascular effects of protarnine sulfate in man. J Thorac Cardiovasc Surg 1982;84:505-514.
Sharath M D, Metzger W J, Richerson H B, Scupham R K, Meng R L, Ginsberg B H, Weiler J M. Prot amine-induced fatal anaphylaxis: prevalence of antiprot amine immunoglobulin E antibody. J Thorac Cardiovasc Surg. 1985;90:86-90.
Sheridan D, Carter C, Kelton J G. A diagnostic test for heparin-induced thrombocytopenia Blood. 1986;67.27-30.
Sherman D G, Dyken M L, Fisher M, Harrison M J G, Hart R G. Antithrombotic therapy for cerebrovascular disorders. Chest. 1989;95(suppl):140S-155S.
Shetty H G, Blackhouse G, Bentley D P, Routledge P A. Effective reversal of warfarin-induced excessive anticoagulation with low dose vitamin $K_1$. Thromb Haemost. 1992;67:13-15.
Shull K C, Nicolaides A N, Fernandes e Fernandes J, Miles C, Homer J, Needham T, Cooke E D, Eastcott F H. Significance of popliteal reflux in relation to ambulatory venous pressure and ulceration. Arch Surg. 1979,114 1304-1306.
Sills R H, Marlar R A, Montgomery R R, Deshpande G N, Humbert J R. Severe homozygous protein C deficiency. J Pediatr. 1984;105:409-413.
Singh A K, Wetherley-Mein G. Microvascular occlusive lesions in primary thrombocythaemia. Br J Haematol. 1977;36:553-564.
Smith V C, Hallett J W Jr. Subclavian vein thrombosis during prolonged catheterization for parenteral nutrition: early management and long-term follow-up. South Med J 1983;76:603-606.
Squires J W, Pinch L W C. Heparin-induced spinal fractures JAMA. 1979;241:2417-2418.
Stamatakis J D, Kakicar W V, Sagar S, Lawrence D, Naim D, Bentley P G. Femoral vein thrombosis and total hip replacement. Br Med J. 1977;2:223-225.
Stein P D, Athanasoulis C, Alavi A, Greenspan R H, Hales C A, Salzman H A, Vreim C E, Terrin M L, Weg J G. Complications and validity of pulmonary angiography in acute pulmonary embolism. Circulation. 1992;85:462-468.
Stein P D, Willis P W III, DeMets D L History and physical examination in acute pulmonary embolism in patients without preexisting cardiac or pulmonary disease. Am J Cardiol. 1981;47:218-223.
Strandness D E Jr, Langlois T, Cramer M, Randlett A, Thiele B L. Long-term sequelae of acute venous thrombosis. JAMA 1983;250,1289-1292.
Stroke Prevention in Atrial Fibrillation Study: final results. Circulation. 1991;84:527-539.
Sumner D S, Londrey G L, Spadone D P, Hodgson K J, Leutz D W, Stauffer E S Study of deep venous thrombosis in high-risk patients using color flow Doppler. In Bergan J J, Yao J S T, eds. Venous Disorders. Philadelphia, Pa.: W B Saunders; 1991:63-76.
Svensson P J, Dahlback B. Resistance to activated protein C as a basis for venous thrombosis. N Engl J Med. 1994;330:517-522.
Szucs M M Jr, Brooks H L, Grossman W, Banas J S Jr, Meister G, Dexter L, Dalen J E. Diagnostic sensitivity of laboratory findings in acute pulmonary embolism. Ann Intern Med. 1971;74:161-166.
Tanaka K, Takao M, Yada I, Yuasa R, Kusagawa M, Deguchi K. Alterations in coagulation and fibrinolysis associated with cardiopulmonary bypass during open heart surgery. J Cardiothorac Anesth. 1989;3:181-188.
Teofili L, De Stefano V, Leone G, Micalizzi P, Iovino M S, Alfano G, Bizzi B. Hematological causes of venous thrombosis in young people: high incidence of myeloproliferative disorder as underlying disease in patients with splanchnic venous thrombosis. Thromb Haemost. 1992;67:297-301.
Teoh K H T, Young E, Bradley C A, Hirsh J. Heparin binding proteins contribution to heparin rebound after cardiopulmonary bypass. Circulation 1993,88(pt 2).II-420-II-425.
Thaler E, Lechner K. Antithrombin III deficiency and thromboembolism. Clin Haematol. 1981,10:369-390.

(56) References Cited

OTHER PUBLICATIONS

The Boston Area Anticoagulation Trial for Atrial Fibrillation Investigators. The effect of low-dose warfarin on the risk of stroke in patients with nonrheumatic atrial fibrillation. N Engl J Med. 1990,323:1505-1511.

The PIOPED Investigators. Value of the ventilation/perfusion scan in acute pulmonary embolism: results of the prospective investigation of pulmonary embolism diagnosis (PIOPED). JAMA. 1990;263:2753-2759.

The urokinase pulmonary embolism trial: a national cooperative study. Circulation 1973;47(suppl 2):1-108.

Thomas M L. Phlebography. Arch Surg. 1972; 104:145-151.

Tibbutt D A, Davies J A, Anderson J A, Fletcher E W L, Hamill J, Holt J M, Thomas M L, Lee G D J, Miller G A H, Sharp A A, Sutton G C. Comparison by controlled clinical trial of streptokinase and heparin in treatment of life-threatening pulmonary embolism. Br Med J. 1974;1:343-347.

Tilney M L, Griffiths H J, Edwards E A. Natural history of major venous thrombosis of the upper extremity. Arch Surg. 1970;101:792-796.

Triplett D A, Brandt J T, Musgrave K A, Orr C A. The relationship between lupus anticoagulants and antibodies to phospholipid. JAMA. 1988;259:550-554.

Triplett D A, Brandt J T. Lupus anticoagulants: misnomer, paradox, riddle, epiphenomenon. Hematol Pathol. 1988;2:121-143.

Turpie A G G, Gent M, Laupacis A, Latour Y, Gunstensen J, Basile F, Klimek M, Hirsh J. A comparison of aspirin with placebo in patients treated with warfarin following heart-valve replacement. N Engl J Med. 1993;329:524-529.

Turpie A G G, Gent M, Laupacis A, Latour Y, Wright D, Hoffman J, Gunstensen J. Basile F, Klimek M, Hirsh J. Reduction in mortality by adding acetylsalicylic acid (100 mg) to oral anticoagulants in patients with heart valve replacement. Can J Cardiol. 1991;7(suppl A):95A. Abstract.

Turpie A G G, Gunstensen J, Hirsh J, Nelson H, Gent M. Randomised comparison of two intensities of oral anticoagulant therapy after tissue heart valve replacement. Lancet. 1988;1:1242-1245.

Turpie A G G, Hirsh J, Gent M, Julian D, Johnson J. Prevention of deep vein thrombosis in potential neurosurgical patients: a randomized trial comparing graduated compression stockings alone or graduated compression stockings plus intermittent pneumatic compression with control. Arch Intern Med. 1989,149:679-681.

Uden A. Thromboembolic complications following scoliosis surgery Scandinavia Acta Orthop Scand. 1979:50:175-178.

Urokinase-Pulmonary Embolism Trial: morbidity and mortality. Circulation. 1973;58:II-66-II-72.

Vandenbroucke J P, Koster T, Briet E, Reitsma P H, Bertina R M, Rosendaal F R. Increased risk of venous thrombosis in oral-contraceptive users who are carriers of factor V Leiden mutation. Lancet. 1994;344:1453-1457.

Verhagen H. Local hemorrhage and necrosis of the skin and underlying tissues at starting therapy with dicumarol or dicumacyl. Acta Med Scand. 1954;148:453-467.

Violi F, Ferro D, Valesini G. Thrombosis in the antiphospbolipid antibody syndrome. N Engl J Med. 1995;333:665. Letter.

Visentin G P, Ford S E, Scott J P, Aster R H. Antibodies from patients with heparin-induced thrombocytopenia/thrombosis are specific for platelet factor 4 complexed with heparin or bound to endothelial cells. J Clin Invest. 1994;93:81-88.

Vogel P, Laing F C, Jeffrey R B Jr, Wing V W. Deep venous thrombosis of the lower extremity: US evaluation. Radiology. 1987; 163:747-751.

Walker M G, Shaw J W, Thomson G J L, Cumming J G R, Thomas M L. Subcutaneous calcium heparin versus intravenous sodium heparin in treatment of established acute deep vein thrombosis of the legs: a multicentre prospective randomised trial. Br J Med (Clin Res Ed). 1987;294:1189-1192.

Warkentin T E, Hayward C P M, Boshkov L K, Santos A V, Sheppard J A, Bode A P, Kelton J G. Sera from patients with heparin-induced thrombocytopenia generate platelet-derived microparticles with procoagulant activity: an explanation for the thrombotic complications of heparin-induced thrombocytopenia. Blood. 1994;84:3691-3699.

Warkentin T E, Kelton J G. Heparin-induced thrombocytopenia. Annu Rev Med. 1989;40:31-44.

Warkentin T E, Kelton J G. Heparin-induced thrombocytopenia: predominance of venous thrombotic complications, and a high risk for subsequent thrombosis in patients who are initially recognized with isolated thrombocytopenia. Blood 1994,84(suppl 1):188A. Abstract.

Warkentin T E, Kelton J G. Interaction of heparin with platelets, including heparin-induced thrombocytopenia. In: Bounameaux H, ed. Low-Molecular-Weight Heparins in Prophylaxis and Therapy of Thromboembolic Diseases. New York, N.Y.: Marcel Dekker Inc. 1994:75-127.

Warkentin T E, Levine M N, Hirsh J, Horsewood P, Roberts R S, Gent M, Kelton J G. Heparin-induced thrombocytopenia in patients treated with low-molecular-weight heparin or unfractionated heparin. N Engl J Med. 1995,332:1330-1335.

Wasserman L R, Gilbert H S. Complications of polycythemia vera. Semin Hematol. 1966;3:199-208.

Weber D M, Phillips J H Jr A re-evaluation of electrocardiographic changes accompanying acute pulmonary embolism. Am J Med Sci. 1966,251:381-398.

Weinberg A C, Lieskovsky G, McGehee W G, Skinner D G. Warfarin necrosis of the skin and subcutaneous tissue of the male genitalia. J Urol. 1983;130:352-354.

Weitz J I, Hudoba M, Massel D, Maraganore J, Hirsh J Clot-bound thrombin is protected from inhibition by heparin-antithrombin III but is susceptible to inactivation by antithrombin III-independent inhibitors. J Clin Invest. 1990,86:385-391.

Wells P S, Brill-Edwards P, Stevens P, Panju A, Patel A, Douketis J, Massicotte M P, Hirsh J, Weitz J I, Kearon C, et al. A novel and rapid whole-blood assay for D-dimer in patients with clinically suspected deep vein thrombosis. Circulation. 1995;91:2184-2187.

Wells P S, Hirsh J, Anderson D R, Lensing A W A, Foster G, Kearon C, Weitz J, D'Ovidio R, Cogo A, Prandoni P, Girolami A, Ginsberg J S. Accuracy of clnical assessment of deep-vein thrombosis. Lancet. 1995;345:1326-1330.

Wells P S, Lensing A W A, Davidson B L, Prins M E, Hirsh J. Accuracy of ultrasound for the diagnosis of deep venous thrombosis in asymptomatic patients after orthopedic surgery: a meta-analysis. Ann Intern Med. 1995;122.47-53.

Wessler S, Gitel S N. Warfarin: from bedside to bench. N Engl J Med. 1984,311:645-652.

Wessler S, Yin E T. On the mechanism of thrombosis. Prog Hematol. 1969,6 201-232.

Wheeler H B, Anderson F A Jr, Cardullo PA, Patwardhan N A, Jian-Ming L, Cutler B S. Suspected deep-vein thrombosis: management by impedance plethysmography. Arch Surg. 1982;117:1206-1209.

Wheeler H B, O'Donnell J A, Anderson F A Jr, Penney B C, Peura R A, Benedict C Jr. Bedside screening for venous thrombosis using occlusive impedance phlebography. Angiology. 1975,26:199-210.

Wheeler H B, Pearson D, O'Connell D, Mullick S Impedance phlebography. technique, interpretation, and results. Arch Surg. 1972;104:164-169.

White C L, Brewer M L, Witte M M, Pond G B. Protean manifestations of pylethrombosis: a review of thirty-four patients. Ann Surg. 1985,202.191-202.

White P W, Sadd J R, Nensel R E. Thrombotic complications of heparin therapy: including six cases of heparin-induced skin necrosis. Ann Surg 1979;190:595-608.

White R H, McKittrick T, Hutchinson R, Twitchell J. Temporary discontinuation of warfarin therapy: changes in the international normalized ratio. Ann Intern Med. 1995;122:40-42.

Wille-Jorgensen P, Christense B W, Bjerg-Nielsen A, Stadeager C, Kjaer L. Prevention of thromboembolism following elective hip surgery the value of regional anesthesia and graded compression stockings. Clin Orthop 1989,247:163-167.

Wille-Jorgensen P, Thorup J, Fischer A, Hoist-Christensen J, Flamsholt R. Heparin with and without graded compression stock-

(56) References Cited

OTHER PUBLICATIONS ings in the prevention of thromboembolic complications of major abdominal surgery: a randomized trial. Br J Surg. 1985,72:579-581.

Wilson J J, Lesk D, Newman H. Subclavian-axillary vein thrombosis: successful treatment with streptokinase. Can Med Assoc J. 1984;130. 891-893.

Wilson J R, Lampman J. Heparin therapy: a randomized prospective study. Am Heart J. 1979;97:155-158.

Wingerd M, Bernhard V M, Maddison F, Towne J B. Comparison of caval filters in the management of venous thromboembolism. Arch Surg. 1978;113:1264-1271.

Wise P H, Hall A J. Heparin-induced osteopenia in pregnancy Br Med J. 1980;281:110-111.

Wise R C, Todd J K. Spontaneous, lower-extremity venous thrombosis in children. Am J Dis Child. 1973;126:766-769.

Yap A S, Powell E E, Yelland C E, Mortimer R H, Perry-Keene D A. Lupus anticoagulant Ann Intern Med. 1989,111 262-263.

Yett H S, Skillman J J, Salzman E W. The hazards of aspirin plus heparin N Engl J Med. 1978;298:1092. Letter.

Young E, Cosmi B, Weitz J, Hirsh J. Comparison of the non-specific binding of unfractionated heparin and low molecular weight heparin to plasma proteins. Thromb Haenost. 1993,70:625-630.

Young E, Prins M, Levine M N, Hirsh J. Heparin binding to plasma proteins, an important mechanism for heparin resistance. Thromb Haemost 1992;67 639-643.

Zauber N P, Stark M W. Successful warfarin anticoagulation despite protein C deficiency and a history of warfarin necrosis. Ann Intern Med. 1986;104:659-660.

Zilliacus H. On the specific treatment of thrombosis and pulmonary embolism with anticoagulants, with a particular reference to the post thrombotic sequelae. Acta Med Scand. 1946;170.1-221.

Zivelin A, Rao L V, Rapaport S I. Mechanism of the anticoagulant effect of warfarin as evaluated in rabbits by selective depression of individual procoagulant vitamin Kdependent clotting factors. J Clin Invest. 1993;92:2131-2140.

Felding et al., "Adjusted-dose Intravenous Heparin Treatment Evaluation of an Automated and Non-Automated Schedule", Thromb. Res., Aug. 15, 1988, 51(4), 447-452.

Oster et al., "A Cost-effectiveness Analysis of Prophylaxis Against Deep-Vein Thrombosis in Major Orthopedic Surgery", JAMA, Jan. 9, 1987, 257(2), 203-208.

* cited by examiner

DEVICE AND METHOD FOR PREVENTION AND TREATMENT OF DEEP VENOUS THROMBOSIS

FIELD OF THE INVENTION

The invention relates to prevention and treatment of deep venous thrombosis through the regional perfusion of antithrombotic agents distal to a compression device.

BACKGROUND OF THE INVENTION

A. The problem

Deep venous thrombosis with the attendant risk of pulmonary embolism and post phlebitic syndrome is a frequent complication in older patients who have undergone surgery, suffered trauma or who have serious illness such as malignancy or sepsis. In any category, patients who are 40 years of age or older are considered to be at greatest risk. Also, the longer the period of immobilization, the greater the risk of DVT. Other factors that have been reported to contribute to development of DVT are obesity, prior history of DVT and smoking. While none of these factors alone or in combination will identify individual patients who will develop DVT, the incidence of DVT during the postoperative or post-traumatic period does correlate with the condition.

DVT has three major risks for the patient, two acute and one delayed. The acute problems are leg swelling, pain and tenderness, and the risk of pulmonary embolism. In pulmonary embolism part of the thrombus breaks away and is carried to the lung where it can block a pulmonary artery causing respiratory distress in proportion to the amount of blockage, i.e., to the size of the embolus. Large emboli that block both pulmonary arteries cause immediate death. The delayed problem is the post phlebitic syndrome in which there is lower extremity pain or cramps at rest, leg edema, skin changes and skin breakdown causing chronic ulcers of the lower extremity. Clinicians have long known that the post phlebitic syndrome develops in a large percentage of patients who have DVT, especially those having extensive thrombus formation. Objective studies have shown that 1-10 years following the occurrence of DVT as much as 80% of patients will have both symptoms and abnormal venous hemodynamics. While the post phlebitic syndrome is less dramatic than a major pulmonary embolus, it is a serious condition for the patients, resulting in much discomfort and expense.

In some patient groups, DVT and pulmonary embolism are major causes of morbidity and mortality. Thromboembolism is a major cause of morbidity and mortality in patients with spinal cord injury. The prevalence of DVT has been reported to range from 47% to 78%. Of these, 1 to 2% will die of pulmonary embolism. Thrombosis usually occurs 1 to 3 weeks after injury, with a peak between days 7 and 9. The incidence of thromboembolic complications in patients undergoing surgery for fractured hip is high, ranging from about 40-60%. In patients undergoing knee arthroplasty the incidence of DVT ranges from about 50% to 85%. In gynecologic malignancy the incidence of DVT was 35%. The incidence of DVT in patients undergoing elective general abdominal surgery was about 9% in those without malignancy and about 11% in those with malignancies.

An understanding of the structure and possible mechanisms of formation of venous thrombi is of direct relevance to the design of methods aimed at preventing their formation or the propagation of thrombi that have formed already.

B. Initiation and Propagation of DVT

Deep vein thrombi vary from a few millimeters in length to long tubular masses that partially or completely fill the deep main veins of the leg. These thrombi start as small nidi and initially grow in size by deposition of successive red and white layers. The white layers are rich in platelets and neutrophils interspersed with fibrin while the red layers contain mostly erythrocytes entrapped in fibrin. Beyond a certain stage of growth venous thrombi become mostly red, resembling clotted blood, i.e. the bulk of a clinically significant thrombus is composed mostly of erythrocytes entrapped in fibrin. Steps and possible mechanisms of initiation and propagation of venous thrombi are as follows:

Step 1. Thrombi are initiated at venous confluences, saccules and valve pockets throughout deep veins of the leg, thigh and pelvis. This suggests that these locations are susceptible to predisposing factor(s). It is possible, even probable, that the structure of veins at these sites is a contributing factor. Veins that have saccules, such as soleal veins in humans are reported to be thin walled and dilated. Jugular veins from dogs that had received an intravenous infusion of the vasodilators bradykinin, histamine or serotonin showed leukocyte infiltrated tears just above valve leaflets. Moreover, in the area of venous confluences the vein wall is dramatically attenuated. This could make these areas susceptible to small tears such as those found at venous confluences in canine veins. Intraoperative venous dilation was observed noninvasively by ultrasound in both animal models and patients undergoing total hip replacement. In animals, dilation correlated with the incidence of damaged confluences and in patients with subsequent development of DVT. Administration of dihydroergotamine plus low dose heparin during the pre- and postoperative period reduced venous dilation and the incidence of post operative DVT. Since these endothelial tears served as sites for accumulation of leukocytes and platelets in animals, they might serve as sites for initiation of thrombosis in humans.

Step 2. Adherent neutrophils and platelets are activated. Separately and in combination they generate/release substances that activate and attract more neutrophils and platelets. The classical example is the release of ADP by platelets. More recently it was discovered that a combination of activated neutrophils and platelets generate neutrophil activating peptide-2 (NAP-2). Cathepsin G (secreted from the granules of activated neutrophils) is capable of converting beta thromboglobulin (BTG) (secreted from alpha granules of platelets) into NAP-2 by proteolytic cleavage of 12 N-terminal amino acids from BTG. NAP-2 so generated could induce secretion of more cathepsin G which would in turn stimulate more platelet secretion, providing more substrate for generation of more NAP-2. This would constitute a positive feedback loop for accumulation of both neutrophils and platelets.

Step 3. Coagulation is initiated and promoted by the mass of activated platelets in the white layer. Activated platelets accelerate coagulation thousands of times by providing a surface for assembly of coagulation protein complexes that are necessary for conversion of prothrombin to thrombin. Activated platelets promote the catalysis of two sequential reactions in the blood coagulation cascade: the activation of Factor X to Factor Xa by a complex of Factors IXa and VIIIa and calcium ions, and conversion of prothrombin to thrombin by a complex of Factors Xa and Va and calcium ions. Platelets possess specific, high-affinity, saturable receptors for Factors Xa, V(Va), VIII, IX and IXa. Platelets are able to amplify minute stimuli to promote the local explosive formation of fibrin. This could lead to the formation of a layer of clot rich in red cells until coagulation was stopped by some as yet undefined mechanism(s). Perhaps the layer of mostly red cells entrapped in fibrin becomes sufficiently thick to physically block further dissemination of thrombin from the activated platelets or perhaps coagulation factors are inhibited.

Step 4. A new layer of neutrophils and platelets are deposited. One mechanism by which this might be initiated is by the binding of neutrophils and platelets to polymerizing fibrin. One might envision that the red layer is formed by rapid coagulation of whole blood so that leukocytes and platelets do not have time to accumulate selectively. As the red layer thickens and coagulation slows down, fibrin protofibrils are exposed at the surface of the red layer long enough to allow leukocytes and platelets to bind and accumulate selectively. Erythrocytes do not bind to polymerizing fibrin as do neutrophils and platelets. As in initiation of thrombi, generation/secretion of active substances would promote accumulation of more cells, ultimately resulting in another cycle of coagulation.

Step 5. After the nidus grows to some critical point, coagulation with entrapment of erythrocytes predominates and forms the mass of the thrombus. It has long been proposed that reduced blood flow in the immobilized patient contributes to initiation and propagation of thrombosis by allowing activated clotting factors to accumulate in the slow moving blood in the deep veins of the legs.

C. Prior Art Clinical Approaches for Prevention of Deep Venous Thrombosis

1. Overview of Prevention of DVT

From the foregoing discussion it is obvious that three characteristics dominate the initiation and propagation of venous thrombosis. First, initiation and propagation are localized to the deep veins of the legs. Second, both initiation and propagation depend on processes that are necessary for defense of the body against trauma and infection. Platelet activation (and accumulation) and blood coagulation are necessary to stop the loss of blood from disrupted blood vessels. Neutrophil response to stimulation is essential for defense of the body against infection. Third, development and propagation of thrombi are complex, involving blood clotting (thrombin generation and action), cellular interactions (platelet-platelet, neutrophil-neutrophil and platelet-neutrophil interactions) and interactions between parts of the clotting mechanisms and cellular interactions.

Initiation and propagation of DVT might be considered to represent an undesirably large response of normal defense mechanisms in the deep veins of the leg. Approaches to preventing DVT must be based on a realization that neither of these processes can be completely inhibited throughout the body for more than a brief time without serious risk of bleeding or infection.

2. Anticoagulants for Prevention of DVT

For about 50 years, efforts to prevent development of DVT and to treat those that do develop have focused on the judicious use of anticoagulants, first through full doses of oral anticoagulants and more recently through low dose heparin prophylaxis. The aim has been to achieve a helpful degree of anticoagulation (prolongation of the clotting process) without causing hemorrhage. Low dose heparin has become the standard of comparison for other preventive methods since it is relatively safe and simple and prevents approximately 65% of subclinical thrombi found by leg scanning after elective general surgery. Postoperative death from pulmonary emboli may be reduced by 65% also.

However, there are clinical situations in which low dose heparin is less effective, most notable after orthopedic surgery where the use of more complex regimens, including adjusted dose heparin and various schedules of warfarin prophylaxis are appropriate. Several studies have shown that higher levels of anticoagulation are more effective than lower ones. However, if anticoagulation is too high, bleeding complications result.

Clinical experience with the use of heparin as an anticoagulant is summarized below. In all cases, standard (unfractionated heparin) or low molecular weight heparin fragments were given subcutaneously once, twice or three times daily. No clotting parameters were measured. DVT was diagnosed by leg scan and in some cases venography.

The results of 24 studies between 1972 and 1979 were summarized by Salzman and Hirsh (1982). A total of 3,899 patients in 15 studies who underwent elective general surgery of moderate severity were given 5000 units of unfractionated heparin subcutaneously every 8 or 12 hours. The incidence of DVT ranged from 5% to 44% in untreated patients and from 1% to 13% in treated patients. In nine studies of 574 patients who underwent elective hip surgery, the incidence of DVT in untreated patients ranged from 37% to 59% and in treated patients from 7% to 46%. In a more recent study of 517 patients undergoing 638 total knee replacements, 49 patients inadvertently did not receive prophylaxis and in 41 (84%) of them ipsilateral deep vein thrombosis developed. The incidence of ipsilateral thrombosis was 57% in the 468 knee replacement patients who did receive prophylaxis. Pulmonary embolism was diagnosed clinically in 1.7% of patients but was suggested in 7% by lung scans.

Low molecular weight heparin, (LMWH), i.e. fragments derived from standard heparin, has received extensive testing in recent years. Patients undergoing general surgery were randomized to either LMWH or placebo. In a study of 4,498 general surgery patients randomized to either LMWH or placebo, there was a statistically significant difference in overall mortality between the groups, 0.8% in placebo and 0.36% in LMWH patients (P<0.05). There was also a significant reduction in thromboembolic mortality, from 0.36% in placebo group to 0.09% in LMWH group. However, there was an increase in postoperative wound hematomas and transfusion requirements in the LMWH group compared to the placebo group. No difference was detected in major bleeding. Ockelford et al (1989) randomized 183 patients to either LMWH or placebo and found that DVT was reduced from 15.9% in the placebo group to 4.2% in the treatment group.

In seven studies in which standard heparin was compared with LMWH in general surgery patients the two types of heparin had the same efficacy in general. In one study bleeding was found to be greater with LMWH while in another it was found to be less. In the other studies there was no apparent difference in bleeding.

In total hip and total knee replacement patients, in whom low dose heparin treatment leaves a high incidence of DVT (around 25%), LMWHs have been tied in three trials in which they were compared with placebo. The incidence of DVT in patients receiving LMWHs was significantly reduced in all three studies. Turpie (1991) found that a fixed dose of low molecular weight heparin (enoxaparin) reduced the rate of DVT from 42% to 12% in a group of patients undergoing elective total hip replacement. Proximal vein thrombi were reduced from 20% to 4%. In a group of 349 patients undergoing total hip replacement those receiving unfractionated heparin had an incidence of DVT of 16% and those receiving low molecular weight heparin had an incidence of 12.6% with the difference not being significant). In both cases the dose was adjusted and no placebo group was included.

In patients undergoing knee arthroplasty or tibial osteotomy administration of a low molecular weight heparin every 12 hours, the incidence of DVT was reduced from 65% in the placebo group to 19% in the treated group, a reduction of 71%. The incidence of proximal vein thrombi was reduced from 19% to none, a reduction of 100%. In patients undergoing elective total hip replacement, a LMWH reduced the incidence of DVT from 56.6% to 15.5%, a reduction of 74%.

In a large study (665 patients) fixed doses of unfractionated heparin and low molecular weight heparin were compared for their ability to prevent DVT in patients undergoing elective total hip replacement. In patients receiving unfractionated heparin the incidence of DVT was 23.2% and in those receiving low molecular weight heparin it was 19.4%. Rates of proximal vein thrombi were detected in 6.5% and 5.4% respectively. The differences were not significant.

At least five different preparations are licensed for clinical use in Europe. Large multicenter trials have been completed in Canada and the United States with promising results. Based on these studies it is probable that low molecular weight heparins will be approved for routine clinical use in North America in the near future.

Because fixed doses of heparin have failed to protect a significant percentage of orthopedic patients from DVT, more aggressive anticoagulation has been tried. The value of increasing the level of heparin anticoagulation in preventing DVT in patients undergoing elective total hip replacement was determined by Leyvraz et al (1983). In a group of 41 patients who received a fixed dose of 3500 U every eight hours 39% developed DVT. In the group of 38 patients who received adjusted dose heparin (APTT 31.5-36 seconds) only 13% developed DVT. No differences in bleeding were found. The efficacy of adjusted versus fixed low dose heparin in prevention of DVT was studied in 100 patients who had hip surgery for hip replacement or fractured neck of femur. Patients were randomized to the two groups. Significant improvement in protection against postoperative DVT was observed in the adjusted heparin group (replacement and fracture patients) (p=0.017).

Other anticoagulants have also been used in patients undergoing orthopedic surgery. Warfarin used as an anticoagulant resulted in a total incidence of DVT of 31% with an incidence of 3% proximal vein thrombosis in patients undergoing total hip replacement. No placebo group was used but these patients usually have an incidence of DVT of around 40% to 60%. Bailey et al (1991) found an incidence of DVT of 26.6% in hip replacement patients receiving low dose warfarin. Coumadin used as anticoagulant in a group of patients undergoing knee arthroplasty resulted in an overall incidence of DVT of 33% with an incidence of thigh vein thrombi of 6%. No placebo group was included but the incidence of thigh vein thrombi of 6%. No placebo group was included but the incidence of DVT in these patients is usually over 50%, sometimes being as high as 85%. The premise has now been established that less than standard doses of warfarin are efficacious. However, the dose of warfarin required to be effective without causing bleeding complications remains to be determined in relevant clinical settings.

The rate of DVT after total knee replacement without prophylaxis has been reported to be as high as 84%. Coumadin anticoagulation and pneumatic calf compression boots have been used in an effort to reduce this rate. In 48 patients receiving coumadine the incidence of DVT was 33% with 29% having calf thrombi and 6% having thigh thrombi. In the boot group (81 patients) the total incidence of DVT was 31% with 27% having calf thrombi and 6% having thigh thrombi. No treatment related complications were reported in either group. Cost analysis showed coumadine to be approximately 50% more expensive than boots.

Patients with spinal cord injury suffer a high incidence of thrombotic complications. Green (1991) randomized 29 patients to receive a fixed dose of 5000 U of heparin subcutaneously every 12 hours compared with an equal number of patients treated with doses of heparin adjusted to prolong the APTT to 1.5 times control values; the mean dose was 13,200 U every 12 hours. Thromboembolism occurred in 31% of those on fixed dose and only 7% of those on the adjusted dose (<0.05). However, 24% of those receiving the higher dose of heparin had bleeding compared to none in the fixed group (p<0.02).

Taken together these studies demonstrates the dilemma that must be faced in administering sufficient heparin to prevent DVT without causing bleeding. They also show that the effectiveness of anticoagulation in preventing DVT does indeed depend on the dose, as would be expected.

3. Inhibitors of Platelet Function Prevention of DVT

Inhibition of platelet activation by aspirin has been tried as a method of preventing DVT. While aspirin is still given to post surgical patients, it is generally recognized that it is not effective. In a double blind randomized trial of patients having surgery after hip fracture the incidence of DVT was 46% in the placebo groups and 42% in the aspirin treated group.

4. Intermittent Pneumatic Leg Compression for Prevention of DVT

Based on repeated observations that the incidence of DVT increased with the length of time the patient was immobilized, it has been accepted that reduced blood flow ("stasis") contributes to the thrombotic process. Therefore, means have been sought to increase blood flow in the legs of immobilized patients. These have included elastic stockings, intermittent pneumatic leg (calf and thigh) compression, passive foot motion and electrical stimulation of the calf muscle.

Intermittent pneumatic leg (calf and thigh) compression was used for preventing DVT after total hip replacement in 311 patients undergoing total hip replacement. DVT was present in 49% of controls and 24% of treated patients, with proximal vein thrombi present in 27% of controls and 14% of treated patients. Bailey et al (1991) found DVT in 6.0% of patients who were treated with sequential compression devices. Gerhart et al (1991) found DVT in 21% of patients who had operatively treated fracture of the hip. In patients undergoing total knee replacement an incidence of DVT of 33% and 19% was found.

Patients who received pneumatic sequential compression of the legs following total hip replacement had an incidence of DVT of 22% and 25%. In patients undergoing total knee replacement the incidence of DVT was 32%. This method, "pressure boots", is used in combination with low dose heparin in two hospitals familiar to the applicants.

Prevention of DVT in patients undergoing major orthopedic surgery is cost effective. Examination by techniques of decision analysis showed the cost-effectiveness of several methods of preventing DVT. The methods included warfarin sodium, low dose subcutaneous heparin, graduated compression stockings, intermittent pneumatic compression, heparin plus dihydroergotamine mesylate, and heparin plus stockings. In untreated patients the death rate was 153 per 10,000 patients. With most prophylaxis, this number was at least halved and the most effective methods may reduce the number of deaths by three fourths. In addition, all of the prophylaxis considered were cost saving: average costs of care being reduced by +19.40 to +181.6 per patient. Throm. Res. 51 (4):447-52, 1988 and JAMA 257(2):203-8, 1987.

5. New Drugs for Prevention of DVT

Standard unfractionated heparin is currently the only agent widely used to prevent and treat DVT in the United States.

However, low molecular weight heparin is used extensively in Europe and Scandinavia (see material presented in prevention and treatment). It is expected that low molecular weight heparin will soon be approved by the FDA for use in the US. Investigation of dermatan sulfate, which as heparin, is a highly sulfated mucopolysaccharide that inhibits blood clotting is not so far advanced.

Another class of possible thrombin inhibitors was suggested by recent studies on the thrombin receptor that is found on cells that are activated by thrombin. Of relevance to the pathogenesis of DVT, thrombin receptors are found on platelets and endothelium. The thrombin receptor has a thrombin cleavage site that accounts for receptor activation. The receptor also has an acidic region with some similarities to the carboxy-terminal region of the leech thrombin inhibitor, hirudin. Synthetic peptides corresponding to the receptor cleavage site (residues 38-45), the hirudin-like domain (residues 52-69) and the covalently associated domains (residues 38-64) were evaluated for their ability to bind thrombin. Peptides 38-45 and 38-64 were competitive inhibitors of the chromogenic substrate activity of thrombin.

The boroarginine peptides are also effective inhibitors of thrombin. Coagulation of plasma (activated partial thromboplastin time) was prolonged at very low (nanomolar) concentrations in vitro. Intravenous administration of boroarginine peptides to rabbits (0.2-2 mg/kg) intravenously or subcutaneously also prolonged the clotting time of plasma prepared from blood removed after the peptide was administered. One boroarginine peptide, Ac(D)-Phe-Pro-bro-Arg effectively inhibited fibrin accretion on an experimental thrombus in the rabbit jugular vein with little systemic anticoagulation. The same peptide (DuP 714) reduced the incidence of thrombosis in a rabbit model of stasis induced thrombosis from 100% to 33%. Kettner et al (1990) suggested that this new class of synthetic thrombin inhibitors may well be clinically useful as antithrombotic agents.

Another group of agents with antithrombin activity are hirudin and its derivatives. Hirudin is a natural thrombin inhibitor derived in small quantity from the saliva of *Hirudinaria manillensis* leeches. Use of recombinant DNA technology has enabled production of large quantities of the protein and development of a number of analogues. These have been used in 161 studies recorded in Library of Medicine as of Jan. 3, 1994. Most of these studies have been on production and characterization of recombinant proteins with a number of studies on their effects in animal models. However, three studies on humans appeared during 1993. One study (Fox et al, 1993) was on a group of human volunteers to determine the overall effects and the effect on blood coagulation and bleeding time and to study the pharmacokinetics behavior of Hirulog (BG8967). A group of 45 patients who were undergoing cardiac catheterization were randomized to receive either heparin or a hirulog as a bolus injection. Hirulog, a direct thrombin inhibitor provided a predictable level of anticoagulation without major hemorrhagic or allergic complications. In another study 291 patients pretreated with aspirin and undergoing elective coronary angioplasty were studied (Topol et al, 1993). Hirulog instead of heparin was administered to five groups in order to study the dose dependent effects of the drug. In each group the patient received the specified bolus of hirulog followed by a 4-hour intravenous infusion. The end point was abrupt vessel closure within 24 hours of initiation of the procedure. Patients in the groups receiving a higher dose of hirulog had fewer closures than those receiving lower doses, thus there was a dose dependent effect. There was only one bleeding complication and no report of adverse physiological or allergic responses. The inventors found no mention of the use of hirulogs for prevention or treatment of DVT but propose that this is a logical extension of these clinical studies.

As mentioned above, the nidus of a thrombus contains layers or zones formed of aggregates of neutrophils and platelets. Without the aggregation of neutrophils and platelets as well as the sticking of the two cell types to each other, the process of thrombus formation would not occur. Recent rapid progress in understanding the mechanisms of the interactions of these two cell types with themselves and with each other suggests new approaches for preventing DVT. One likely approach is the development of drugs that interfere with the action of "selectins" a group of receptors that are found on endothelium (E- and P-selectin), leukocytes including neutrophils L-selectin) and platelets (P-selectin).

The selectins are single polypeptide chains with external domains composed of three types of smaller domains that resemble other proteins. The N-terminal end of the peptide is a calcium requiring lectin-like domain. This is followed by an epidermal growth factor domain and variable numbers of complement regulatory protein-like repeating units. All three selectins are heavily glycosylated. This property is proving to be of great significance in their function.

In all three families, some receptors are present on the cell surface constitutively while in other cases stimulation of the cell is required for surface exposure or activation of the receptor. There are two means for stimulating exposure of receptors. In one case stimulation causes the exposure of preexisting receptors within seconds or minutes while in other cases receptors must be synthesized de novo, a process requiring a few hours. In still other cases activation of the cell apparently causes a change in conformation of existing, inactive receptors so that they become active.

L-Selectin is constitutively expressed on PMN and participates in PMN-EC recognition/adhesion. Monoclonal antibodies to L-selectin inhibit PMN localization at sites of acute inflammation in vivo and block PMN binding to cytokine-activated EC in vitro. L-selectin appears to be a major ligand (or receptor) involved in leukocyte rolling along veins in thin membranes. This is the earliest event in leukocyte adhesion observed in many studies of ethin membranes over the years. In a rabbit model monoclonal antibodies against L-selectin inhibited up to 80% of intravascular leukocyte "rolling". Interestingly, L-selectin interacts with E-selecting and P-selectin to produce PMN binding to EC. L-selectin is shed, probably by proteolytic cleavage, from both PMN and lymphocytes after cellular activation). This down regulation of L-selectin suggests that it might be necessary to inhibit neutrophil adhesion for a relatively short time during and after an operation to prevent their binding to the vein.

Platelets, as EC have P-selectin in their granules. This can be translocated to the surface during stimulated secretion and is responsible for adhesion of stimulated platelets to PMN. This is most likely of major importance in the early development of thrombi since platelet/neutrophil masses form the nidus of thrombi.

Small carbohydrates modeled on the structure of the carbohydrate residue that confers activity and specificity on a group of receptors (selectins) found on platelets, neutrophils and endothelium are being used in experimental inflammation and metastasis and may be applicable for use in preventing or treating DVT. Administration of all of these inhibitors by a route that increased their concentrations in the blood of deep leg veins would increase their inhibitory activity locally while minimizing undesirable effects systemically.

Despite the progress that has been made in reducing the incidence of DVT, a sizable percentage of patients undergoing major orthopedic and gynecological operations as well as those sustaining spinal cord injury still develop thromboembolic complications including DVT, pulmonary embolism and the postphlebitic syndrome. Moreover, there are some patient groups in whom low dose heparin has not been successful. These include intracerebral hemorrhage in which low dose heparin was ineffective. Patients undergoing radical prostatectomy had an incidence of 11% pulmonary emboli. This was reduced to none in patients receiving mini-dose heparin but bleeding complications in the treated group were unacceptably high. These observations clearly indicate that better prophylaxis is needed.

D. Treatment of Existing DVT

The classical treatment of DVT is the use of intravenous heparin. Adjusted dose intravenous heparin given by continuous infusion for the initial treatment of patients with proximal vein thrombosis resulted in an incidence of 6.9% of new episodes of venous thromboembolism. Major bleeding associated with initial therapy occurred in 5% of these patients. No placebo group was possible.

The efficacy and safety of adjusted subcutaneous heparin was compared with continuous intravenous heparin as the initial treatment for acute deep vein thrombosis. In both groups heparin was adjusted to maintain the activated partial thromboplastin time between 50-70 seconds. There was no significant difference between the two groups in the rate of new pulmonary embolism. Five of 47 in the subcutaneous group and 5 of 49 in the intravenous grouped developed pulmonary embolism (10.6% and 10.2% respectively). Similarly there was no difference in the rate of hemorrhagic complications (9.8%).

Unfractionated heparin was administered subcutaneously in doses adjusted according to the activated partial thromboplastin time (1.5-2 times pretreatment values). There was improvement in {fraction (32/66)} 48% of patients but an increase in thrombus size in {fraction (12/66)} 18%. One symptomatic non-fatal pulmonary embolism and one major bleeding episode occurred. In a similar study Prundoni et al (1992) found that 14% of 85 patients suffered recurrent venous thromboembolism diagnosed objectively. A similar study found that adjusted dose intravenous standard heparin improved the mean Marder score in 61% of 49 patients.

These studies show that treatment of existing DVT with heparin administered intravenously or subcutaneously are ineffective in upwards of 50% of patients and that many patients develop hemorrhagic complications.

SUMMARY OF THE INVENTION

Deep venous thrombosis is a common and serious pathological event which most frequently occurs in the small veins of the distal lower extremity and which can result in venous thromboembolism with definite potential for life threatening pulmonary embolization and for long term disabling lower extremity chronic venous insufficiency syndrome. Treatment and prevention of deep venous thrombosis requires administration of antithrombotic agents in doses sufficiently high enough to prevent clotting. The appropriately high concentrations can be effective but can cause hemorrhage which is a serious clinical problem. The novel method described here is regional perfusion of antithrombotic agents which provides for exposure of tibial and soleal veins of the lower extremity to high concentrations of antithrombotic agents and with lower systemic concentrations of antithrombotic medication. Thus, the complications of effective doses of antithrombotic agents for prevention or treatment of deep venous thrombosis can be minimized or averted by the regional perfusion of medication administered distal to a compressive device capable of diversion of venous drainage into the deep venous system and concomitant delivery of antithrombotic agents into the venous plexus of prime clinical concern.

In particular, the invention relates to a device for compressing the superficial veins of a patient's foot including an inflatable pedal venous stocking having a window to provide dorsal pedal access for venous puncture for administration of an anti-coagulant or other drug or dye and an inflation device connected to the inflatable stocking for inflating the inflatable stocking to an air pressure sufficient to compress the superficial veins of the patient's foot. In an exemplary embodiment, the inflatable pedal venous stocking extends from the patient's toes to a point above the patient's malleolus, although the inflatable pedal venous stocking may extend from the patient's toes to a point approximate the level of the patient's knee. The inflatable pedal venous stocking may include straps that are adjustable to facilitate positioning of the patient's foot in the inflatable pedal venous stocking and to hold the inflatable pedal venous stocking in place during inflation and drug or dye delivery. The inflatable pedal venous stocking also may include an inner bladder for accepting air and a lateral supramalleolar luer-lock port for connection to the inflation device.

In accordance with another exemplary embodiment, the invention includes a device for compressing the superficial veins of a patient's foot including a pedal venous stocking having a window to provide dorsal pedal access for venous puncture for administration of an anti-coagulant or other drug or dye and at least one adjustable pressure strap that has an elastic gauge scale for use in adjusting the strap so as to provide a compressive force sufficient to compress the superficial veins of the patient's foot. In this embodiment, the pedal venous stocking also extends from the patient's toes to a point above the patient's malleolus or to a point approximate the level of the patient's knee. The window provides a port over the dorsum of the foot. VELCRO™ may be used for securing the pressure strap with the requisite tension to compress the superficial veins of the patient's foot.

The invention also includes a method of delivering an antithrombotic drug into the deep veins of a patient's leg, comprising the steps of providing venous cannulation in the dorsum of the patient's foot for application of the antithrombotic drug and applying pressure to the patient's foot proximal to the venous cannulation and up the patient's foot in an amount sufficient to compress superficial veins of the patient's foot. The antithrombotic drug may be an anti-coagulant such as unfractionated heparin or low molecular weight heparin. The step of applying pressure may comprise the step of inflating an inflatable pedal venous stocking on the patient's foot to an air pressure sufficient to compress the superficial veins of the patient's foot, where the inflatable pedal venous stocking has a window to provide dorsal pedal access for the venous cannulation. The step of applying pressure may also comprise the step of adjusting an adjustable pressure strap of a pedal venous stocking on the patient's foot so as provide a compressive force sufficient to compress the superficial veins of the patient's foot, the adjustable pressure strap having an elastic gauge scale for use in adjusting the strap until the compressive force is achieved. The method of the invention may also include the further step of injecting the antithrombotic drug into alternating web spaces of the distal foot while the pressure is applied so as to compress the superficial veins of the patient's foot.

These and other characteristic features of the invention will be apparent from the following detailed description.

DETAILED DESCRIPTION OF EXEMPLARY EMBODIMENTS

Figure 1:
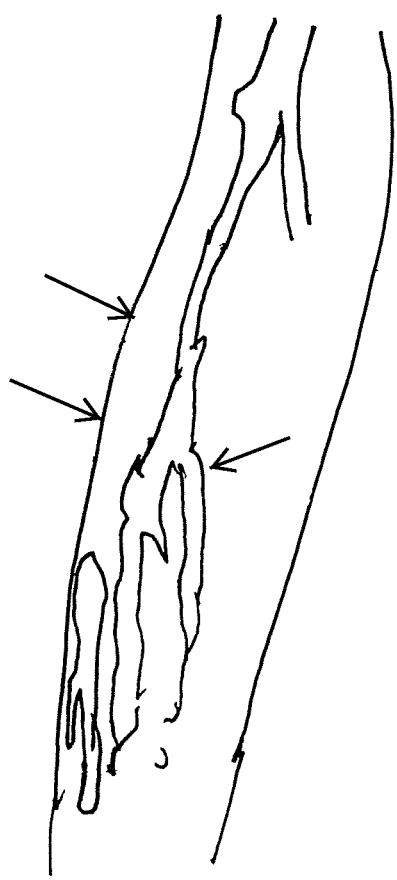
FIG. 1 illustrates a venograph of a deep vein thrombosis (DVT) in the veins of the leg.

The current application describes a preferred embodiment for preventing development of DVT and for treating patients who do develop this complication. The preferred embodiment includes a novel method of administering drugs that prevent DVT from forming or preventing the extension of those that have formed. Standard heparin is currently the only agent approved for such use in the United States. However, approval of low molecular weight heparin is expected soon. Other anticoagulants such as thrombin receptor analogs, boroarginine peptides and hirulogs show promise and could be administered by the same route. Analogues of selectins that inhibit neutrophil, platelet and endothelial adhesive receptors are another group of new and potentially useful agents. These also could be administered by the novel route proposed in this application.

The preferred embodiment for means of administration of these inhibitors into the foot are described below. The preferred embodiment for new means of administering antithrombotic agents would provide a higher concentration in the deep veins of the legs than in the systemic circulation.

The preferred embodiment is based on the essential characteristics of the processes involved: 1) the localization of the thrombotic process to deep veins of the legs; 2) the complexity of blood clotting and cellular interactions involved and 3) the necessity for these body defense mechanisms to retain some degree of function systemically. It also takes into account the facts that blood clotting and cellular interactions can be inhibited in a dose dependent fashion and that a higher level of anticoagulation is more effective but causes more hemorraghic complications.

Since venous thrombosis is localized to deep veins in the legs and since blood clotting and cellular interactions can be inhibited by several agents in a dose dependent manner, it is intuitively obvious that maintaining a higher level of inhibitor in the leg veins than in the general circulation would allow the degree of inhibition to be greater locally than systemically. This would provide an opportunity to prevent or retard development of thrombi in deep veins while lowering the risk of bleeding or infection systemically. The preferred embodiment for prevention and treatment of DVT introduces the administration of heparin or other inhibitors into the foot in such a way that the agent goes into the deep leg veins, thereby providing a higher concentration of inhibitor in these veins than would be found in the systemic blood.

Heparin or other inhibitors would be administered by continuous intravenous infusion or by subcutaneous injection into sites in the foot while the superficial venous and lymphatic systems of the lower leg are collapsed. The simplest way to direct heparin or other inhibitory agent into the deep veins of the legs would be by pressure tourniquet or by pressure boots. Extensive venography has shown (FIG. 1) that contrast dye injected into a vein on the dorsum of the foot is directed into the deep veins of the leg when sufficient pressure is applied to the leg to collapse the superficial veins. It was estimated that the concentration of material in the leg veins was as much as 100 fold higher than that in the general circulation. This indicates that heparin or other antithrombotic drugs injected into the foot would also be directed into the deep leg veins when sufficient pressure is applied to collapse the superficial leg veins. A similar magnitude of concentration of heparin or other inhibitor in leg vein blood as compared to the general circulation can be expected.

Devices for Compression of Superficial Veins in Foot and Calf

Compression of the superficial veins of the foot and calf will shift the blood that normally flows in these veins to the deep veins of the calf. Since reduced blood flow in the deep veins of the calf is accepted as a contributing factor in the development of DVT, increasing the blood flow is an accepted means of reducing the risk. Compressing the superficial veins and shifting blood flow to the deep veins of the calf is an essential element of the proposed new method for preventing or treating DVT.

The preferred embodiment of preventing or treating DVT provides a means for obtaining a local high concentration of antithrombotic drugs in the deep veins of the calf of the leg. These deep veins (see FIG. 1) of the calf are the sites for initiation of DVT in most cases. These veins are the soleal, peroneal and tibial plexes. A high local level of antithrombotic drugs will be obtained by administration into a superficial vein on the dorsum of the foot to the deep veins in the calf. It will be necessary to have a means of compressing the superficial veins so that the drugs are shunted into the deep veins by the superficial to deep venous communicating veins (FIG. 1). For this gentle controlled, uniform pressure will be applied to the foot and if desired a uniform or graded pressure to the calf of the leg. Administration of antithrombotic drugs will need to be continued at least for many hours and in some cases for several days.

For this, a specially constructed device will have multiple clinical applications other than delivery of antithrombotic drugs. All embodiments of the air inflatable (FIG. 2) and the elastic strap/strip devices (FIG. 4) will be useful in routine ascending venography. They will increase patient comfort during the procedure by replacing the narrow tight tourniquet that is now used. They will reduce the painful post-venography sequella by preventing prolonged retention of contrast material in the superficial veins. Lingering intravenous contrast causes endothelial irritation resulting in phlebitis in the foot and leg. This troublesome condition is associated with erythema, pain, tenderness, swelling and localized hyperthermia in the area distal to the type of tourniquet currently in use. This post-injection reaction of iodine contrast for venography can occasionally lead to extension into ascending deep venous thrombosis and, most commonly, troublesome long-term symptomatic superficial venous fibrosis and smoldering inflammatory activity of the veins of the dorsum of the foot.

For the case of the application of this invention as an aid to clinical venography, its design will alleviate stasis of contrast, subsequent to injection, and its associated sequella, namely regional superficial stasis phlebitis in the foot and distal leg caused by lingering intravenous contrast and the venous endothelial irritation and reaction in the region of the injection reaction. This troublesome condition is associated with erythema, pain, tenderness, swelling and localized hyperthermia in the area distal to the type of tourniquet currently in use which techniques do not provide gentle, consistent, thorough regional superficial venous compression, as is well known in the art. This post-injection reaction of iodine contrast for venography can occasionally also lead to subsequent extension into ascending deep venous thrombosis and, most commonly, troublesome long-term symptomatic superficial venous fibrosis and smoldering inflammatory activity of the veins of the dorsum of the foot.

In paralyzed and other patients who require long-term care these devices can be used with convenience and patient comfort. The inventors know of no prior or existing art that offers the advantages of user convenience and inexpensive construction for obtaining a specified level of pressure and a high degree of patient comfort.

Figure 2:
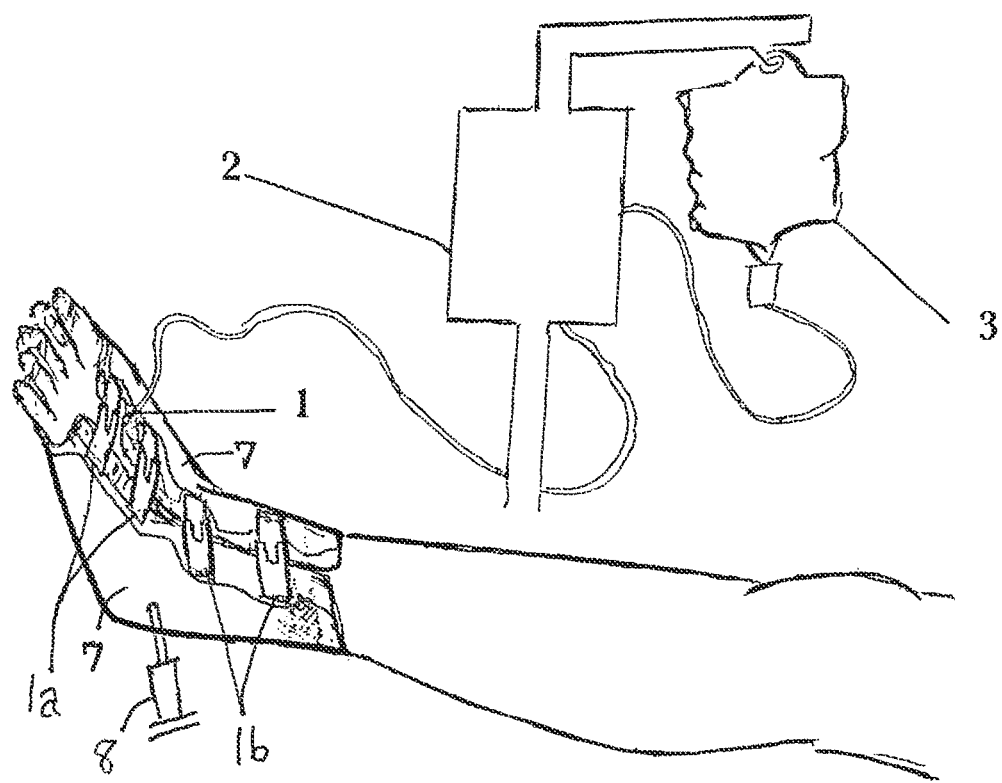
FIG. 2 illustrates a pneumatic venous compression device with a supramalleolar and pedal compression.

Air inflatable superficial venous compression devices 1 as shown in FIG. 2 are made in a short (above the ankle, i.e., supramalleolar level) and a long (just below the knee) version to meet the needs of different clinical situations. Both versions (embodiments) will be made in small, medium and large to accommodate the large range of sizes the feet and legs of patients. Both embodiments will be constructed with an outer and an inner layer, described below. Both the short and long embodiments will have a port to provide access to the dorsum of the foot. Because the size of the foot and the pattern of superficial veins will vary among patients, the port will be sufficiently large to expose a considerable part of the dorsum of the foot. The part of the port (opening) that is not needed will be closed by VELCRO™ straps 1a. As shown in FIG. 2, at least two such straps is will be provided, the cephalad (proxial) strap will be carried over the intravenous access, and the caudad (distal) strap will be carried under the intravenous access tubing. The margin of the port will be reinforced to aid the straps 1a in guaranteeing full compressive force over the foot in the area of the port. This will provide compression of the superficial veins despite the opening in the device 1. Both the short and long embodiments will have an opening on the medial side to allow for putting on and removing the device. The opening will be closed with a zipper or VELCRO™ ships 1b.

The outer layer of both embodiments will be composed of firm, flexible but relatively non elastic woven fabric. This outer material is lined with an inner bladder which can be inflated to the desired pressure, suggested as 40 mmHg. Materials that are known to the art will be used for construction of both long and short embodiments of the device.

Figure 3:
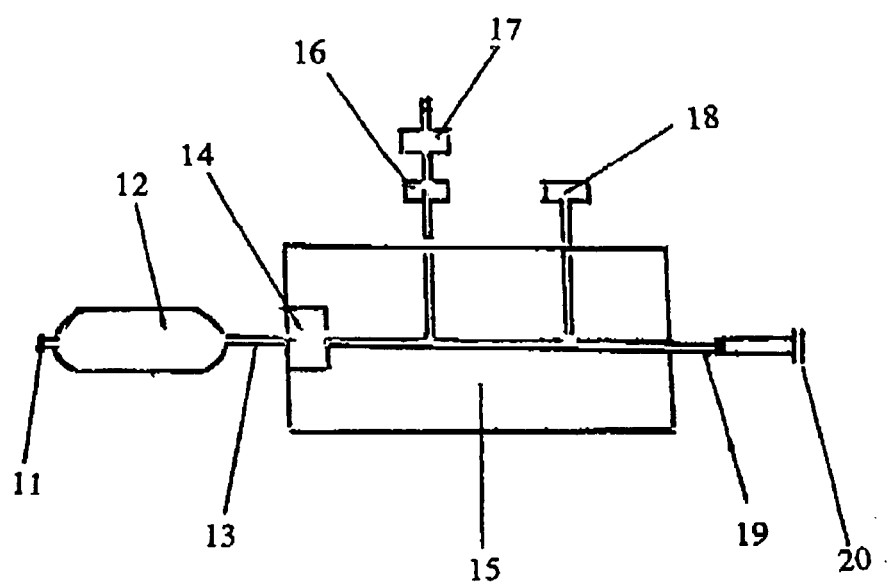
FIG. 3 illustrates a pneumatic compression regulator that allows air to enter but prevents air from escaping.
Figure 5:
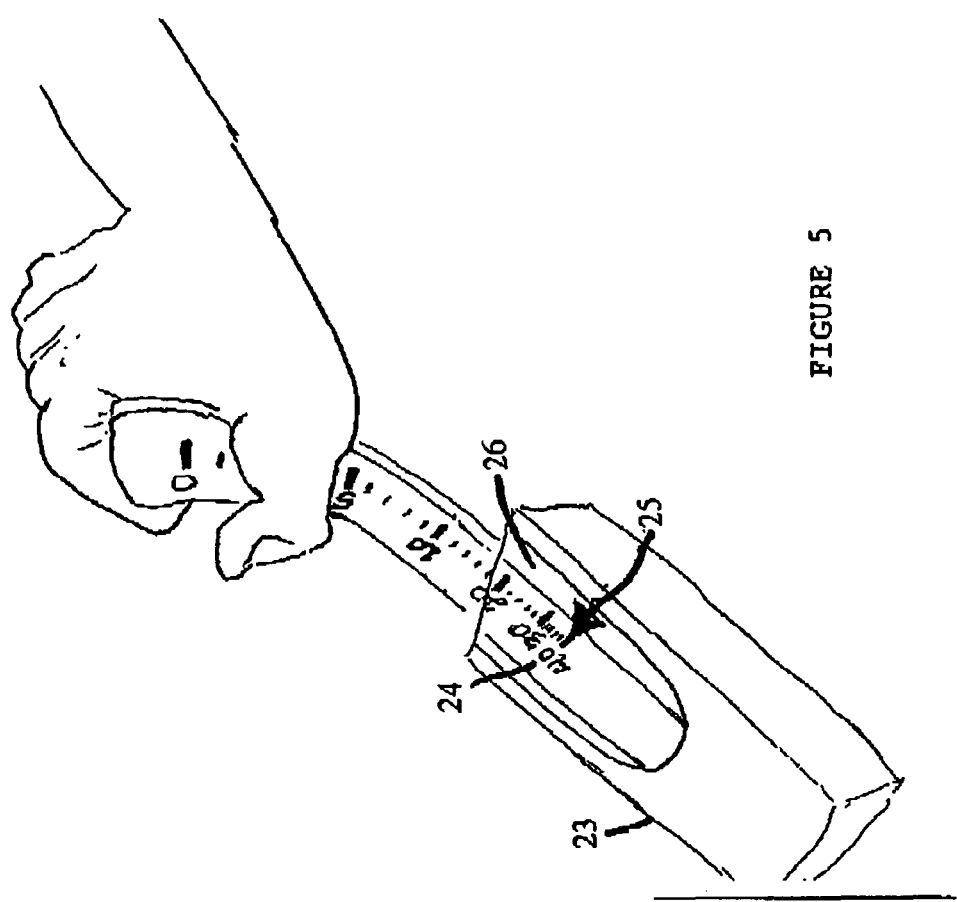
FIG. 5 illustrates a device for adjusting the pressure applied by the device of FIG. 4.

Two versions are described, one with a fixed pressure of 40 mm/Hg and one with variable pressure. In both versions pressure will be attained by inflation of the inner bladder with a hand compressible elastic bulb with a single one way valve for inflation. A separate valve will be provided for deflation. In the fixed pressure version, an escape valve set at 40 mm/Hg will be provided. This pressure has been shown to be sufficient to compress superficial veins. The variable pressure model will be provided with a pressure gauge as shown in FIG. 5. Hereafter the bulb with or without the gauge will be referred to as the pneumatic compression regulator. The pneumatic compression regulator is shown in FIG. 3. This is a modification of the pneumatic compression regulator described in U.S. Pat. No. 5,108,456 (Apr. 28, 1992). Details of the regulator of FIG. 3, including the operation of elements 4-10, can be found in U.S. Pat. No. 5,108,456 and such description is hereby incorporated by reference.

The air inflatable device 1 shown in FIG. 2 compresses the superficial veins of the foot from the toes to approximately four inches above the malleolus. The pneumatic venous compression device of FIG. 2 provides supramalleolar and pedal compression. The connection of the extension tubing into an intravenous catheter is a Leur-Lok connection, and the self-adhesive material on the anterior device cleavage is similar to VELCRO™. There is dorsal pedal access for venous puncture and intravenous Heparin or contract (venogram dye) administration. The margin of the cleavage is enforced and surfaced anteriorly with self-adherent material similar to VELCRO™. The straps 1a are removable for easy versatility in positioning following the preferred entry point of administering the venapuncture. The delivery pump 2 is capable of a range of delivery volumes from the fluid-medication reservoir 3. The air inflatable pedal compressive device 1 is constructed with an inner bladder 7 and lateral supramalleollar Luer-Lok port 8 to allow temporary, intermittent inflation to a known adjustable air pressure. The modified pedal venous stocking has an enforced window for intravenous access, no inflatable bladder, especially designed pressure controlled straps and a gentle foam-type inner lining material.

FIG. 3 illustrates a pneumatic compression regulator having a one-way valve 11 that allows air to enter the squeeze bulb 12. Squeeze bulb 12 is connected by tubing 13 to a second one-way valve 14 that allows air to enter but prevents air from escaping. An exchange line 15 that has a normally closed exhaust valve may be opened by digressing the extension 16 using an adjustable relief valve 17 to provide a known pressure. The source is attached via connecting conduit 18 to connecting joint 19 similar to a fluid tight Luer-Lok 20 commonly used to provide easy attachment and detachment.

Figure 4:
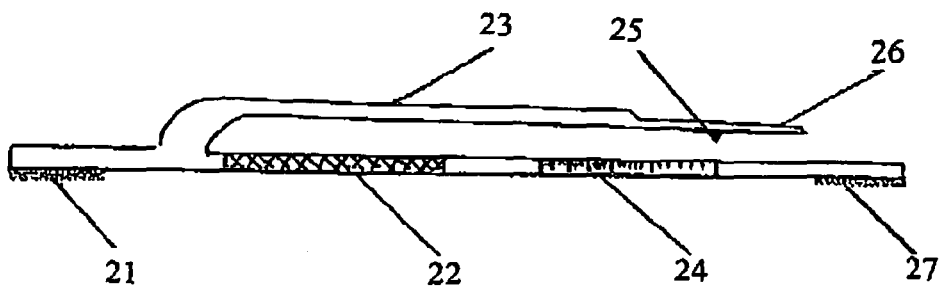
FIG. 4 illustrates a pressure-strap regulated device with an elastic gauging scale that compresses the superficial veins of the foot from the toes to approximately four (4) inches above the malleolus.

FIG. 4 illustrates an adjustable strap for a stocking embodiment with a spanning window having a port in the dorsum of the foot. VELCRO™ allows for optimal positioning. A similar window opening strap is used for the boot embodiment in which the tension adjustment device may be omitted. The strap of FIG. 4 is secured by VELCRO™ 21, 27 on both ends. The elastic strap 22 provides the tension. The housing 23 provides a stationary support against which the tension can be measured in the graduated logarithmic scale 24 compared to the stationary indicator arrow 25 and visualized through a transparent portion 26 of the housing 23.

FIG. 5 provides a view of the adjustable strap used in the stocking embodiment of FIG. 4, in a semi-stretched state as ideal pressure equivalent tension is being achieved just prior to the applicator's affixing of the velour portion of the strap in position. This device compresses the superficial veins of the foot from the toes to approximately four inches above the malleulus or may extend to approximately the patient's knee.

A commercially advantageous (cost-saving) feature is a mechanism whereby the entire pneumatic compression regulator device may be detached from the compressive device at a point external to a one-way valve. This allows proper, safe consistent inflation without the need for the patient to lie with the valve fixed to the stocking. This will provide comfort to the bedridden patient and will allow the patient to change lying position readily without injury caused by the presence of the attached apparatus. In addition, this would reduce the cost since this part of the device could be used with more than one patient.

This system of obtaining and maintaining pneumatic pressure will be applicable to other devices for application to the leg or arm.

It will be desirable to interrupt the intravenous infusion of heparin for short periods as the patients become ambulatory. For this reason, the inflatable bladder will not extend under the sole of the foot so as to avoid interference with walking. In one embodiment the inflatable bladder will stop short of the dorsum of the foot while in another it will extend to the end of the device in which case access to the dorsum of the foot will be provided by a port in the bladder.

Superficial venous compression devices with elastic gauging scale have some characteristics in common with the air inflatable compression devices 1 of FIG. 2. They also will be made in a short (above the ankle, i.e., supramalleolar level) and a long (just below the knee) version to meet the needs of different clinical situations. The long version will be made with two different systems of closure: a set of VELCRO™ straps or a continuous VELCRO™ strip. The design of such embodiments is shown in FIGS. 4 and 5.

The inner lining of the stocking version of FIG. 4 is 1.5 to 2.0 cm circumferentially. This lining allows for consistent compression of the superficial veins over both the eminences and recessions of the surface topography of the foot, transmitting the 30-50 mm Mercury pressure within an acceptable range of pressure from the distal transmetatarsal level to the supramalleolar level. The outer encasing material is a flexible but relatively inelastic woven fabric within which the foam can be compressed to transmit the required pressure. The pressure compressing the inner foam lining is transmitted from the adjustable straps. There are four straps, measuring 1.5 cm. by 0.5 cm. The elastic portion of the straps has a known elasticity, which is predicated by the elastic coefficient, the thickness and the width wherein the latter two parameters are known determinable values by virtue of laboratory testing and manufacture. The proximal two (supramalleolar) straps are affixed to the medial aspect of the medial margin of the compressive device whereas both medial and lateral margins of the dorsal pedal aspect of the device are variably positionable (removable at each margin) by virtue of its VELCRO™ surfaces 21 and 27 at both ends of the straps. The proximal two straps 21 and 27 have VELCRO™ only at the medial aspect of the straps and are permanently affixed at the lateral ends. This ultimate flexibility of the two distal straps insures ultimate flexibility in conforming to the position of the Heparin lock which is predicated by the variations seen in each individual case. This establishes a dynamically variable and repositionable access port window. The compression devices as referred to herein describe both the embodiments of the compressive stocking and inflatable boot in regards to the positionability or lack thereof of both boot and stocking embodiments.

The inventors know of no existing prior art which offers the advantages associated with both user convenience and inexpensive construction in combination with an enforceable variably adjustable pressure application which is a known advantage of the various pneumatically inflatable boots. Such advantages have ramifications to patient comfort where excess pressure need not occur as well as possible long-term clinical applications other than deep venous thrombosis prevents, where accurate pressure control is advantageous.

By the same mechanism, it should be noted that distinct advantage can be seen with the use of the compressive stocking of the invention in lieu of torniquetion for venography, thereby insuring patient comfort by more consistently substantially reduced compressive force in lieu of a high pressure localized constrictive force.

In addition, the device of the invention eliminates a specific complication of venography, post contrast injection superficial venous pedal phlebitis. Superficial phlebitis by current technique is induced by injecting contrast into the distended superficial venous plexus of the dorsum of the foot distal to the constricting proximal tourniquet. This creates stasis of the irritating contrast substance and causes endothelial initiative reaction and superficial phlebitis, which may result in a chronic smoldering inflammatory response and possible extension into deep venous thrombosis. The invention prevents this complication by compressive occlusion of the superficial veins and thereby eliminates stasis of contrast in the venous system, which would otherwise result from truncated occlusion of the superficial venous tourniquet occlusion.

All embodiments will be made in small, medium and large to accommodate the large range of sizes of patients. Both embodiments will be constructed with an outer end an inner layer, described below. Both the short and long embodiments will have a port to provide access to the dorsum of the foot. Because the size of the foot and the pattern of superficial veins will vary among patients, the port will be sufficiently large to expose a considerable part of the dorsum of the foot. The part of the port (opening) that is not needed will be closed by VELCRO™ straps. At least two such straps will be provided, the cephalad (proximal) strap will be carried over the intravenous access, and the caudad (distal) strap will be carried under the intravenous access tubing. The margin of the port will be reinforced to aid the straps in guaranteeing full compressive force over the foot in the area of the port. This will provide compression of the superficial veins despite the opening in the device.

The outer layer (shell) of both embodiments will be composed of firm, flexible but relatively inelastic woven fabric. The inner layer (lining) will be composed of a layer of soft foam approximately 1.5-2.0 cm thick. This lining will allow for compression of the superficial veins over both the eminences and recessions of the surface of the foot and calf, uniformly transmitting the selected range of pressure (30-50 mm/Hg).

The shell will be constructed of two sections. One section will extend from the knee or above the ankle to just below malleolar level. The other will extend the length of the foot and will cover part of the dorsum, the sides and the sole. The two sections will be attached across the back and the sides to the malleolus. Thereafter they will be separate. The top section will be attached so that one side is longer than the other in order to provide an overlap. This is necessary in order to adjust the device to the leg of the patient. Pressure and closure will be obtained by adjusting the elastic closure devices.

A novel means of providing both closure and adjusting pressure will be provided as shown in FIGS. 4, 5. This is incorporated to allow the clinician or nurse to use constant pressure or to vary the pressure gradient to promote venous return.

In the short version, four straps will be used. Two straps will be used for obtaining closure and pressure of the part of the device above the malleolus. The opening (port) in the foot section of the shell will be closed by two straps that have VELCRO™ on both ends. This provides a means by which the pressure can be adjusted by adjusting the position of the straps. The straps will be triangular in shape with the base of the triangle attached to the device.

In the long version, the device will extend to the level of the knee and will be fitted with a minimum of three additional straps.

In another embodiment of the long version of the device, a continuous closure will run the length of the shell on the medial side. Again the elastic element will be attached to the shell of the device and the strip (VELCRO™ or other material) will be attached to the elastic element. The elastic plus VELCRO™ strip will be used for closure and for obtaining pressure. This variation insures consistent pressure at all levels of the device and implies an improvement over the multiple strap variation by eliminating the possibility of inconsistencies in pressure between the straps.

The long version of both the strap and strip embodiments provides the options of having uniform or graded pressure (FIG. 5) over the calf. With the strap embodiment the pressure at each strap (level) can be adjusted. With the strip embodiment, graded pressure can be obtained by tapering the overlap of the strip. Current literature indicates that graded lower leg compression may augment the effectiveness of low dose heparin and suggests that the same will be true for other antithrombotic drugs.

Despite some of the known negative effects of using tourniquet and particularly of these above mentioned disadvantages with use in venography, two of the significant advantages of the invention are simplicity (in use) and cost. As a result, a simple tourniquet is described that can be used to the greater safety and comfort to the patient by allowing the clinician to spot check the applied pressure during or after application. The present inventive concept is based upon a similar principle as that of the elastically gauged strap feature of the stocking embodiment described above. The tourniquet described herein involves essentially the use of a clamped-on (or otherwise attached) windowed scale gauge which is geometrically calibrated and thus achieves a substantially similar functional objective and mechanism to that of the pressure gauging scale of the stocking embodiment described with respect to FIG. 5 in as much as the transparent window contains the scale which is from the viewers perspective superimposed over a reference marker by which the measured pressure is read. In other words, the numeric scale (FIG. 5) which is physically associated with the transparent window is read by the relative position of the reference marker in relation to relatively extensible overlying numeric scale which changes (i.e., increases) with the degree of tension to which the tourniquet is physically stretched when applied to the patient. This geometrically calibrated scale printed upon the segment ideally ranges from 0-60 mmHg. Almost all clinical applications which use this general type of tourniquet require an applied pressure within this range in order to retain clinical efficacy. In the manner thus described a phlebotomist may, while tightening in the process of tying the device, quickly spot check the estimated approved pressure before committing application of the pressure as estimated. Such a clinical procedural enhancement would likely be a potentially very useful adaptation to the long standing and currently held procedure regimen for tourniquet application.

In one possible alternative embodiment a similar, however quite comparable degree of accuracy could be similarly achieved to that of the primary embodiment whereby the tourniquet essentially utilizes consistently and continuously spaced markers associated with the substantial portion comprising the body of the tourniquet (e.g., the medial 75% portion of the body of the tourniquet) with each segment occupying the lateral portions of the device (e.g., the lateral 12% portions on either end) are occupied by a numbered geometrically calibrated scale similar to that of the fixed position scale of the straps of the stocking embodiment. The essential difference from that of the original preferred embodiment occurs in the clinician's method of implementation which involves after affixing the procedure of tying the tourniquet manually pulling into position one of the lateral segment gauging scales zero points flush to the position of any one of the taught medical markers (the entire lateral segment on either end of which is the untaught portion i.e., the free end). Once the tension level of the tourniquet is checked, the nurse or clinician may readjust accordingly until the desired tension (in mmHg) is achieved. It should be noted that one fundamental distinction between the presently disclosed enhanced method and apparatus and all other and currently known prior art involves the fact that these currently recognized and established compressive devices are generally used extra operatively and in patients with existing predisposing risk factors. These devices are designed functionally to preventing pooling of venous blood to thus help reduce the incidence of the troublesome substantially less severe superficial venous phlebitic syndrome as well as to improve lymphatic return often thereby also improving heart function. One more directly pertinent piece of prior art involves one application of the sequentially inflatable hip boot to the patient's' legs particularly during the post operative period which is intended to reduce the incidence of deep venous thrombus formation. This device is well known to be uncomfortable due to the proximally directed sequential constrictive compressions that must be powerful enough to mobilize deep venous pooled blood which lies beneath the major muscular structures of the lower extremity and cumbersome as well as somewhat commercially impractical for clinical situations in light of an only moderate success level with respect to the overall clinical scope of the problem at hand.

To the best of the inventor's knowledge, there is in the current state of the art no known procedure or apparatus for the implementation thereof for substantially preventively reducing or eliminating the occurrence of deep vein thrombosis post operatively. Because there is an inherent degree of elasticity throughout the body of the entire device (not just at one short segment as in the strap embodiment) an overall substantial elastic displacement (stretch) of the device may represent substantially much smaller relative displacement over any given increment such as the distance between two of the markers which are measured against the geometrically calibrated pressure determination scale, thus the geometrical calibrated scale must, by necessity, occupy a much reduced linear distance by contrast to that of the elastic strap embodiment variation of the present invention disclosure which accordingly must be appropriately considered, for the sake of ease and convenience as well as prevention of errors. In a further convenience enhanced variation (for the benefit of the clinician) color-coded segments superimposed upon a geometric scale indicate critically significant ranges of pressure which may define an appropriate particular application. This feature may also overcome to a certain extent the problem of legibility with regards to the scales occupying a relatively short linear span. It should be noted that the above described color coding feature may also be advantageously applied to the elastic strap variation as well for similar reasons of benefit those above described. There are several distinct advantages for various applications of a readily calibratible tourniquet as described and as would be apparently obvious to a skilled healthcare provider or other form of skilled clinician.

The pressure straps or strips with gauging scale innately possesses broad commercial value in that the use of this inexpensive and convenient user friendly device is designed to assure accurate physician-recommended pressures for the plurality of therapeutic variations for which medical stockings are currently used. The invention can be directly applied to venography in any situation including postoperative and routine venograms. The same technique can be used for regional thrombolytic agents (Streptokinase, Urokinase or other compounds) low-dose regional perfusion. The most likely circumstance would be to treat early known deep venous thrombosis.

Modified elastic stocking as superficial venous compression devices are the simplest and least expensive embodiment of the devices for compressing the superficial veins of the foot and calf. However, they do not provide means for measuring or adjusting the pressure applied to the foot and calf. This device will be made by installing a port in an existing graded elastic stocking, so that the dorsum of the foot can be exposed. The construction and closure of the port is the same as that for air inflatable and elastic strap/strip closure devices described above.

Clinical experience with angiography has shown that material infused into a superficial vein on the dorsum of the foot can be directed into the deep veins of the legs if the material is infused distal to the application of sufficient pressure to collapse the superficial veins. This concentrates the infused compound in the deep veins up to 100 fold the concentration that would be obtained by systemic administration. Concentrating the infused antithrombotic drug in the deep veins of the legs would be an obvious advantage in both preventing development of DVT and treating preexisting DVT. Preventing development of DVT prevents the risks of the patient having a pulmonary embolus or developing the postphlebitic syndrome. Preventing growth of a deep vein thrombus that developed prior to start of treatment reduces the risk of pulmonary embolism and the postphlebitic syndrome since the risk of both conditions increases with the size of the thrombus.

For both prevention and treatment of DVT, by heparin or other antithrombotic drug, the agent is to be infused into a superficial vein on the dorsum of the foot distal to application of sufficient pressure to compress the superficial venous system. This will provide a high local concentration of antithrombotic drug for preventing or treating deep vein thrombosis. A higher dose of antithrombotic drug may be required for treatment than for prevention. Concurrent with the infusion of antithrombotic drug, pressure is to be applied to foot and calf if desired. Pressure will be applied by one of the devices described above. Access to the veins in the dorsum of the foot will be provided by the port in the device.

The patient will be fitted with the compression device and the pressure adjusted to that judged most appropriate by the attending physician. This will be elevated by about 15 degrees.

The protocol for intravenous administration of antithrombotic solutions can be developed by methods known in the art. For example, an intravenous solution containing 10,000 international units of heparin in 500 cc of fluid may be prepared by methods known in the art. This intravenous solution is administered at a volume rate of between about 19 and 31 cc/hr to provide a dose of between about 900-15,000 U per 24 hours. In a preferred embodiment, the volume rate of this solution is about 20 cc/hr to provide a dose of about 9600 U heparin per 24 hours. An infusion pump may be used for accurate volume administration.

A method for delivery of a high level of antithrombotic drug into the deep veins of the leg in accordance with the invention includes the following steps: providing venous cannulation in the dorsum of the foot of patient and applying pressure to the foot proximal to the venous cannulation and/or to the leg up to the level of the knee, in an amount sufficient to compress superficial veins. In immobilized patients, antithrombotic agent may be injected into alternating web spaces of the distal foot with the above described compressive device engaged.

An anticoagulant drug is infused according to dosage and duration of administration that are at the time accepted clinically. This includes but is not limited to unfractionated heparin, low molecular weight heparin, including, but not limited to enoxaparin sodium (Lovenox), hirulogs, thrombin receptor peptides, boroarginine peptides, analogs of selectins and other agents that may inhibit coagulation or platelet and neutrophil accumulation in thrombi into the deep veins of the legs.

The regional perfusion employed in the above described methods for preventing deep venous thrombosis, thereby reducing the risk of pulmonary embolism and postphlebitic syndrome may be utilized in one or both legs as clinically indicated. Further variations and modifications of the aforementioned can, of course, be made without departing from the spirit and scope of the invention as disclosed herein, and those skilled in the art will recognize multiple utilizations of the present invention that are within the scope of this disclosure.

EXAMPLE

Two bags each containing an intravenous solution of 5% dextrose in water and approximately 10,000 international units of heparin are prepared. A small bore (20-22 gauge) polyethylene catheter is inserted into the vein plexus on the dorsum of each foot of the host. A local anesthetic, for example, ½% xylocaine may be administered prior to inserting the catheter. The catheter is then secured and the intravenous solution administered at a volume rate of approximately 19-31 cc/hr, preferably about 20 cc/hr into each lower extremity via an infusion pump. Infusion of heparin or other antithrombotic drug will be continued substantially continuously for as long as clinically indicated. For surgical patients, infusion may be initiated just prior to or after surgery and continued for at least 24-72 hours post-operatively. Infusion may be continued beyond 72 hours if clinically indicated.

While standard heparin was used in the above detailed description of administering antithrombotic agents, the same methods can be used for administering low molecular weight heparin and other antithrombotic drugs such as those mentioned in the background.

It is, of course, relevant within the spirit of the presently disclosed system and method that though at the time of the writing of this disclosure Heparin and Low molecular weight Heparin were by far the prevailing drugs of choice in the preventative treatment of DVT, it would be obvious to one skilled in the art that with appropriate clinical and physiological adaptation to the present protocol herein disclosed that potential future drug analogs in the Heparin class of pharmacological agents (as well as potentially other classes as well) could be efficaciously and prudently used in such fashion, so as to exploit the same physiological advantages of the present pharmacological delivery regimen over that of the prior art which uses the present novel principle of regional perfusion to the target regions of the peripheral venous system responsible for DVT.

In an alternative embodiment, heparin may be administered by injection with a one and one half inch 23 gauge needle into the soleal muscle directly which would provide direct regional and evenly sustained controlled outflow (as is a characteristic feature of the intramuscular injection approach) of heparin into the soleal venous plexus which is the known venous drainage for the principle culprits of the origin of DVT. The preferred administration calls for 2000 to 2500 units every 12 hours bilaterally by nurse or clinician. Duration of administration is substantially identical to that of intravenous pedal administration. No monitoring of PTT or PT is necessary because of the low dose regionality without a substantial effect on overall levels systemically. It should be noted that in this embodiment there is no apparent need for the herein described pedal compression boot. Possible consideration may be given in light of the current research literature for additionally using the graded compression stocking for the prevention of venous stasis. Disadvantages of this approach include at least training of personnel for administering procedure and potential for muscle hematoma which should be self-limiting with termination of treatment or reversion to one of the alternate approaches herein described. In the case of prolonged treatment regimens, possible ensuing inflammation and resulting hematoma may be a primary concern. For this reason at the discretion of the clinician, varied directional approaches of the heparin injection may be utilized. Finally, in order to prevent ensuing leakage of the Heparin following each injection resulting from retrograde flow through incompetent perforating veins proximal to the site of injection, external compression is recommended at the clinician's discretion for patients suspect for predisposition to this potential problem. An alternative application of the above treatment regimen is the treatment of established diagnosed deep venous thrombosis. Unlike that of the preventative approach 5000-8000 units every 12 hours are administered in the higher dose ranges monitoring PIT at certain intervals may be done at the clinician's discretion (which is also applicable for all other herein described variations of administration for controlling the treatment dosage). The duration for administering the treatment regimen may be prolonged depending on the clinical needs and efficacy with regards to the clinical developments thereof.

In yet another alternative embodiment, Heparin is administered into a suitable site of the soft tissues of the distal foot (distal to the pedal compressive boot) which is in this application used so as to guarantee delivery of Heparin into the deep venous (rather than superficial venous or superficial lymphatic) system. Because a venous access port is unnecessary in this application the enforced window as part of the pedal compressive boot or stocking described herein may be deleted from the device. As with that of the other embodiments described the recommended dosage is 2000-2500 units of Heparin at 12 hour intervals bilaterally. It should be noted that in any one of these embodiments both dosage and frequency may be varied within certain limits according to clinical judgment. The preferred sites of soft tissue injection into the foot are the web spaces which can be advantageously alternated to minimize repeated insult to the tissues resulting from frequent injections. Injection is performed with a 1 or 2 cc syringe and a 25 gauge needle. The needle and the injection must be put into the middle of the web space and the track of the needle must be directed proximally between the neurovascular bundles so as to avoid the digital neurovascular bundles. As with the other presently described alternative approaches the use of the present approach is equally well suited for use as a treatment regimen for confirmed DVT as well as the recommended higher dosage ranges mentioned and if recommend by the clinician also in connection with PTT monitoring as well. For extensively prolonged treatment regimens dosage levels may be modified to minimize tissue trauma at the discretion of the clinician or use of alternating regimens wherein varied forms of Heparin are used may be considered as well in combination with the aforementioned approach of alternating the web spaces. The cases comprising the largest demand for use of this treatment are patients with spinal cord injury, particularly paraplegics, and long-term convalescent patients. The extent that the dosage can be reduced and still provide effective deep venous thrombosis prophylaxis has not yet been established. However, in addition to reduction in dosage levels, an alternative approach to administering this group is the utilization of the entire plantar surface wherein altered varied sites may be readily used for each injection. (Full exposure of the plantar surface is achieved by pulling down the distal end of the stocking or removing the stocking upon each administration). It should be noted that this approach would not be practical in an ambulatory patient due to the compounding tissue insult from walking. It is likely under this regimen that most patients should be able to adapt to this form of administration indefinitely especially in light of a somewhat reduced dosage program. It should also be noted that there is a substantial clinical need which is widely recognized with regards to the above group particularly in spinal injury patients in as much as due to the overwhelmingly high percentages of DVT cited in this group even low dose Heparin treatment is far from being a satisfactory resolution for adequately reducing this group's morbidity statistics. It should also be noted that for this approach because there is no need for a dorsal pedal access port (as required for the continuous venous perfusion approach as previously described) the exclusive role of the herein described windowed pedal compression boot as the sole dependable acceptable compressive tunic for applying the necessary compressive force of 40 mmHg. to substantially the entire foot does not apply in this regard in as much as a modified traditional compressive stocking with the distal tip removed which allows for full open exposure of the pedal digits and their corresponding intervening web spaces would be a reasonable alternative for the present approach provided that the substance of the distal portion of the foot is compressively covered so as to avoid swelling in the area of the exposed region.

In light of the above concern, an alternative embodiment for a stocking involves utilization of either a traditional type compressive stocking or that of the pressure gauged elastic strap variation (which as previously described above may be used as is, however, more preferably without the enforced dorsal access window) for better enforced control of the ideal applied pressure. If, however, in accordance with the preferences of the hospital staff or clinician the device of choice is the traditional type compressive stocking, an enforced slit may be utilized in the stocking directly over (i.e., substantially over the level and somewhat narrower than the span of) the underlying web spaces. Ideally this slit is lined by a reinforced dual seam margin which minimizes the likelihood of a somewhat compromised (reduced) pressure application in the area of the slit or distally therefrom while worn. To further assure that this is the case, a single button may also be utilized which is positioned in the middle of the slit in order to provide both the continued compressive force in the toe region as well as convenient access to a nurse or clinician to the web spaces at the times of administration. Immediately prior to injection into the web space of choice the attending nurse may after detaching the button stretch the distal tip of the stocking until the underlying digits thereof protrude so as to provide adequate accessibility to the intervening web space. In an alternative embodiment (an additional modification) of the traditional compressive stocking the stocking is designed such that there is no enclosed or tapered distal end. Instead the distal portion is designed as such an open tubular configuration which extends somewhat beyond the level of the digits so as to allow in this variation both patient comfort with even compressive force over the entire foot as well as ease of access to the web spaces or plantar surface by the nurse or clinician just prior to administering the Heparin injection by inverting and peeling back the end of the stocking (extended) sleeve so as to expose the web spaces or (if desired) the entire remaining portion of the foot without the obvious inconvenience to the patient and attending nurse of having to fully remove then replace the stocking before and after injection respectively.

In all of the above described alternative approaches to delivering Heparin into the deep venous system for prevention as well as treatment it should be noted that because of the recent study trials indicating the inherent multifold benefits low molecular weight Heparin (LMWH) to be used in lieu of standard Heparin for all similar applications that LMWH may be used alternatively wherever standard Heparin is indicated, notwithstanding the fact as is known in the art that an enforced ratio of dosage for standard heparin may be used to calculate the corresponding adjusted dosage whenever LMWH is indicated by the clinician for use as a substitute for that of the standard Heparin regimen (this adjustment ratio is derived on the basis of several considerations including those of faster absorption rate, lower clearance time by the lever and greater potency by weight) differences in clearance time from the body.

Transdermal heparin administration may be achieved using an externally applied patch which may be directly analogous to other transdermally applied patches such as those used for nitroglycerin, scopolamine and nicotine application. The prior art describes the dosage parameters and basic construction of the device which includes a backing layer, a drug reservoir, a rate controlling membrane, contact adhesive and protective peel strip. It is believed that the low molecular weight variety Heparinoid falls within the limits of the molecular weight threshold for transport across a cell membrane. Though the molecular size is probably larger than similarly applied drugs, and may result in slower transdermal delivery, this regional perfusion approach which is used should more than compensate for this factor.

In the preferred clinical application for patients at high risk for deep venous thrombosis, the transdermal patch is applied to the skin of the dorsal aspect of the pedal skin, prior to application of the compressive stocking (which as previously described insures the substantial redistributing of drug laden blood to flow to the deep venous tributaries of the lower extremity). Alternatively, at the clinician's discretion the heparin patch may be used in the sequence of a compressive stocking. Therefore, because an adequate quantity of pedal blood makes its way to the deep venous system the heparin patch may, in certain situations, become a substitute to that of superficial graded compression especially in clinical situations involving long term sedation or a previous history of phlebitis. Use of topically applied heparin to the dorsum of the foot can be considered without the concomitant use of the compressive boot or graded compression in situations where the use of the boot is precluded by leg wound ulceration, neuropathy or the patient's refusal or discomfort.

Clinical applications include surgical and post surgical patients as well as long-term convalescent and cancer patients, convalescent stroke and accident related hemi- or quadriplegia. The clinical application is in the domain of deep venous thrombosis prevention. The efficacious advantages of the invention are ease and comfort of application, low cost and avoidance of immobility, which is a problem with Heparin lock infusion, and length of active drug absorption.

The clinical regimen calls for periodic application of heparin patch. Low molecular weight heparin will require more frequent replacement of the patch due to higher absorption rates, while the higher molecule weight will provide slower released dosage and may be sustained for a longer duration.

ALTERNATIVE EMBODIMENTS

As with other transdermal drugs, the vehicle for administration may be different. For example, drug laden pastes may be applied under a gauze bandage, for direct dermal application in the form of an ointment or the drug in liquid form which may be used to saturate an absorbent medium or gauze covering. Also, as previously described, alternative antithrombogenic drugs (non-heparinoid) currently under investigation may show promise for the transdermal approach by virtue of their lower molecular weight properties (thus facilitating absorption through the skin). Regarding the alternative variation of the drug in the form of a topical ointment, the heparin would be incorporated with a hydrophobic base, which would be topically administered in frequent and profuse quantities. Such topical application in a partially compressive fashion may provide the further benefits of optimizing dermal contact even as the drug becomes absorbed and its relative concentration decreases as well as increased relative pressure differential between the absorbent medium and the skin which may further facilitate transdermal drug transport.

Finally, an alternative method would involve impregnation of Heparin within a dissolvable hardened substrate which potentially may, be well suited for subdermal administration primarily for longer term clinical situations so as to provide a guaranteed delivery of the drug. In addition because such techniques as those above suggested, reportedly only enables a limited degree of permeability of such otherwise sub-optimal permeability, larger molecule weight moieties such as Enoxaparin, the use of such a transdermal device covering as large a region of the foot and/or ankle as is practically feasible may be duly indicated. It should be noted, that as this present description indicates, application to the skin of the distal lower extremity is ideal considering the relatively high molecular weight of the Heparin moiety and consequent relative low absorption rate which may be compensated for by the concentrative effect of regional perfusion.

Alternatively, however, it may be determined through clinical studies that the various above-described procedures may show clinical benefit if applied to the external surface of the abdomen (as a direct replacement for currently administered subcutaneous Heparin). The level of clinical benefit may be improved through the use of the lowest molecular weight anti-thrombogenic drugs currently available or currently under investigation. In any event, given a fixed absorption rate, transdermal delivery rate may be increased as well through use of patches covering a larger surface area of the patient's skin. It can be appreciated that alternative transdermal drug delivery techniques such as those above suggested are (as indicated in the case of the primary disclosed embodiment) in no way intended to be limited to use within the context of delivery of heparin or heparin analogs exclusively that is if and when use of such alternative drug classes become discovered and clinically accepted for use within the present application. When considered in the context of the heretofore other proposed alternative embodiment involving the use of ultrasonic transdermal delivery, it will become apparent that each of the various alternative embodiments above suggested (and potentially others) could be further readily adapted for clinical use if administered in combination with these ultrasonic transdermal delivery techniques. Because they would aptly provide a facilitatory role in drug delivery, it would be appropriate for example, while providing treatment for a specific clinical objective and situation at a specific level of aggressiveness and quantity of target drug delivered to modify the quantity, concentration and/or duration (if periodic) of topically delivered drug compensate appropriately for the increased absorptive rate achieved by virtue of the incorporation of ultrasonic transdermal facilitation into the present indicated protocol. A given transdermal delivery protocol may become adapted as a viable alternative treatment approach for clinical situations which indicate a more aggressive drug delivery approach and as a consequence such an adaptation of the technique to the new clinical situation may be perhaps achievable by virtue of integrating such proposed ultrasonic drug delivery techniques into the otherwise less aggressive transdermally delivered treatment protocol such as those alternative embodiments herein suggested.

Because the energy levels of the ultrasonic transducer device is of a relatively low intensity level, the use of ultrasound techniques may be an alternative embodiment facilitating absorption. At the time this application is written such techniques are in clinical investigational stages and possibly in limited clinical use. The use of this type of device in form of a patch-like device for transdermal delivery of compounds are currently on display at the Tech Museum Innovation in San Jose, Calif.

The suggested methods exemplified herein by the presently proposed alternative embodiments have been provided herein in order to exemplify and elucidate the substantial range of alternative clinical treatment approaches each of which may be potentially viable and perhaps most efficacious for each of the comparably varied range of differing clinical situations (wherein the myriad array of differing clinical situations must be considered whose needs vary in accordance with differing treatment variations in the preventative approaches to DVT). For example, these may span the spectrum from more aggressive treatment protocols as in more acutely immobile patients to those less aggressive treatment approaches for more moderate degree of need for clinical treatment intervention. Thus, the presently suggested alternative embodiments are herein provided accordingly and in no way are intended to limit the broad scope of the claimed inventive concepts or the potential incorporation of as yet unforeseen or future clinical situations, pharmacological agents and/or their associated indicated treatment protocols. This may be particularly true if/when newly discovered techniques become clinically adopted and accepted for transdermal drug delivery. For example, in addition to (or with appropriate modifications, in conjunction with) ultrasonic transdermal delivery, non-syringe based pressure injection drug delivery methods for delivery of pharmacological agents are yet still another technique which has been discovered relatively recently and discussed and tested to a limited degree in clinical situations and thus could form the basis for an alternative delivery device to the above syringe-based delivery approach as embodied herein. Likewise, in the case of alternative (or future alternative) drugs and classes thereof as aforementioned, for delivery via the primary embodiment or utilizing any of the variety of alternative delivery modalities such as those above described, it is worthy to note that such various other classes of drugs could potentially become discovered and incorporated in wide scale clinical use within a relatively short time frame. In particular, recent advances in proteinomics for use in drug discovery are creating a whole new generation of super drugs and drugs whose, behavioral properties (and conceivably even, size) could be customized to a particular clinical situation, or even individual patient. It is also possible that more highly specialized drugs may suggest the possibility of new opportunities by which they could also be delivered in combinatorial fashion if the combined effects are desirable and safe. For example, one could easily consider the possibility in this newly emerging environment of designer drugs for which different properties are desirable and efficacious for particular types of clinical situations requiring DVT prevention. This also does not preclude the possibility of providing these associated desired properties through the administration of the relevant associated drugs in combination with one another.

Some of these properties may include (but are not limited to):

1. Heparin-like anti-thrombogenic properties.
2. Very small molecular weight (e.g., whereby the "target receptor" interacting portion of the agents' molecular moiety could be isolated and thus significantly reduce the molecular size of the molecule to within the range needed for a readily transdermally absorbable drug.
3. Vasoactive properties, as indicated above, such as can be exhibited with dihydroergotamine mesylate which possesses such properties and has been shown to provide further incremental advantages over that of a standard low molecular weight analog in deep venous thrombus prevention when administered in combinatorial fashion with low molecular weight Heparin compared to the use of LMW Heparin by itself. Invariably higher concentration levels of drugs possessing such vasoactive properties which are achievable via the presently disclosed methods for regional perfusion to the lower extremity could further reduce the risk of DVT by further decreasing stasis of pooling deep venous blood. In this alternative embodiment, the preferred delivery protocol as herein suggested indicates an approximately similar relative percentage concentration of dihydroergotamine to LMW Heparin as that relative concentration used in the above referenced experiment conducted by Gwendolyn Stewart (or appropriately adjusted concentrations of any other vasoconstrictive pharmacological analog of preference). The present low molecular weight properties of dihydroergotamine provide one distinct advantage which is its absorptive properties when administered transdermally.
4. Anti-inflammatory properties—This characteristic of a drug would server potentially useful benefits:
   a. Avoiding or minimizing the inflammatory response to the delivery site subdermally.
   b. Reducing the inflammatory response to the drug at or near the endothelium of the venous wall which could activate leukocyte and/or platelet aggregation activity (certain particular consideration to the negative effects of inflammatory response to certain drugs should be considered, for example, as may be relevant to the administration of vasoconstrictors).
5. Properties which are selectively activated in response to certain discreet physiological or biochemical processes such as the aggregation of platelets, or leukocytes or the "clotting cascade" and its associated enzymatic activity.
6. Simply agent-related properties, which interrupt the biochemical process which enables platelet aggregation to occur.

Advantages of Protocol

This novel approach to deep venous thrombosis prevention provides some definite inherent advantages over the traditional approach to anticoagulant therapy, including:

1. Avoid frequent monitoring of prothrombin and partial thromboplastin times;
2. Traditional heparin can be administered at a much lower cost;
3. Anticoagulants can be administered at home;
4. Higher tissue levels localized to treatment area;
5. Less medication needed;
6. Reduced cost of personnel to administer treatment;
7. Possibly reduce hospital length of stay for high risk patients, e.g., following major extremity orthopedic surgery; and
8. Reduced cost also related to ability to substitute heparin therapy for Lovenox therapy with substantial drug savings.

What is claimed:
1. A method of delivering an antithrombotic drug into deep veins of a leg of a patient, comprising the steps of:

providing venous cannulation in a dorsum of a foot of the patient for application of said antithrombotic drug into superficial veins of the foot of the patient;

inflating an inflatable pedal venous stocking configured to extend from toes of the patient to at least a point above a malleolus of the patient to an inflation pressure that causes the inflated pedal venous stocking to apply a uniform pressure to the foot of the patient sufficient to compress superficial veins of the foot of the patient; and injecting said antithrombotic drug into the superficial veins of the foot of the patient or via alternating web spaces of the foot of the patient while the pressure is applied to the foot of the patient by said inflated pedal venous stocking whereby said antithrombotic drug is shunted to deep veins of the leg of the patient via the compressed superficial veins of the foot of the patient.

2. A method as in claim 1, wherein the antithrombotic drug comprises an anti-coagulant.

3. A method as in claim 2, wherein the anti-coagulant is unfractionated heparin or low molecular weight heparin.

4. A method as in claim 1, wherein the step of providing venous cannulation comprises accessing the superficial veins of the foot of the patient via a window of the inflatable pedal venous stocking configured to provide dorsal pedal access for the venous cannulation.

5. A method as in claim 1, wherein the step of inflating the inflatable pedal venous stocking comprises the step of adjusting at least one adjustable pressure strap of said inflatable pedal venous stocking on the foot of the patient so as provide a compressive force sufficient to compress the superficial veins of the foot of the patient, the adjustable pressure strap having an elastic gauge scale for use in adjusting the strap until the uniform pressure is achieved.

* * * * *